(12) United States Patent
Bozkurt et al.

(10) Patent No.: US 10,481,506 B2
(45) Date of Patent: Nov. 19, 2019

(54) METHOD OF MEASURING A STRUCTURE, INSPECTION APPARATUS, LITHOGRAPHIC SYSTEM AND DEVICE MANUFACTURING METHOD

(71) Applicant: ASML Netherlands B.V., Veldhoven (NL)

(72) Inventors: Murat Bozkurt, Uden (NL); Maurits Van Der Schaar, Eindhoven (NL); Patrick Warnaar, Tilburg (NL); Martin Jacobus Johan Jak, 's-Hertogenbosch (NL); Mohammadreza Hajiahmadi, Rotterdam (NL); Grzegorz Grzela, Eindhoven (NL); Lukasz Jerzy Macht, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/967,861

(22) Filed: May 1, 2018

(65) Prior Publication Data

US 2018/0321599 A1     Nov. 8, 2018

(30) Foreign Application Priority Data

May 8, 2017 (EP) .................................. 17169918
Nov. 21, 2017 (EP) .................................. 17202806

(51) Int. Cl.
*G03F 7/20*     (2006.01)
*G01N 21/47*     (2006.01)
(Continued)

(52) U.S. Cl.
CPC ..... *G03F 7/70633* (2013.01); *G01N 21/4788* (2013.01); *G01N 21/9501* (2013.01);
(Continued)

(58) Field of Classification Search
CPC .............. G03F 7/70633; G03F 7/7085; G03F 7/70616; G01N 21/4788; G01N 21/956
See application file for complete search history.

(56) References Cited

U.S. PATENT DOCUMENTS 7,046,361 B1    5/2006   Yang et al.
2006/0033921 A1   2/2006   Den Boef et al.
(Continued)

FOREIGN PATENT DOCUMENTS

EP        3 336 605 A1    6/2018
WO   WO 2013/178422 A1   12/2013

OTHER PUBLICATIONS

International Search Report from related International Patent Application No. PCT/EP2018/059606, dated Jul. 17, 2018; 4 pages.

*Primary Examiner* — Deoram Persaud
(74) *Attorney, Agent, or Firm* — Sterne, Kessler, Goldstein & Fox P.L.L.C.

(57) ABSTRACT

An overlay metrology target (600, 900, 1000) contains a plurality of overlay gratings (932-935) formed by lithography. First diffraction signals (740(1)) are obtained from the target, and first asymmetry values (As) for the target structures are derived. Second diffraction signals (740(2)) are obtained from the target, and second asymmetry values (As') are derived. The first and second diffraction signals are obtained using different capture conditions and/or different designs of target structures and/or bias values. The first asymmetry signals and the second asymmetry signals are used to solve equations and obtain a measurement of overlay error. The calculation of overlay error makes no assumption whether asymmetry in a given target structure results from overlay in the first direction, in a second direction or in both directions. With a suitable bias scheme the method allows overlay and other asymmetry-related properties to be mea- (Continued)

Figure 1:
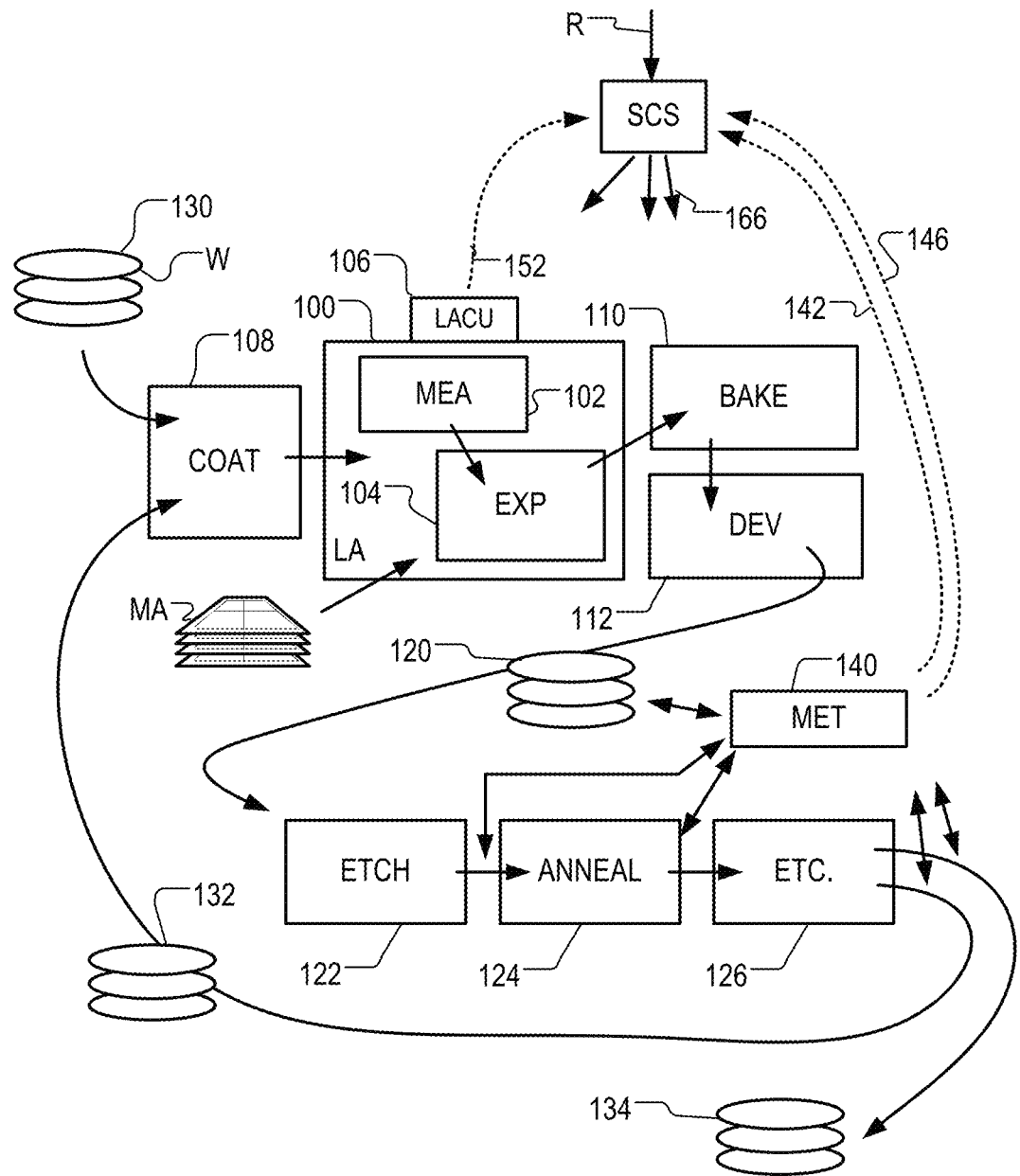

sured accurately, even in the presence of two-dimensional overlay structure.

24 Claims, 14 Drawing Sheets

(51) Int. Cl.
    *G01N 21/956*    (2006.01)
    *G01N 21/95*     (2006.01)
(52) U.S. Cl.
    CPC ......... *G01N 21/956* (2013.01); *G03F 7/7085* (2013.01); *G03F 7/70616* (2013.01)

(56) References Cited

U.S. PATENT DOCUMENTS

| | | |
|---|---|---|
| 2006/0066855 A1 | 3/2006 | Boef et al. |
| 2007/0291269 A1 | 12/2007 | Van Der Schaar et al. |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0123581 A1 | 5/2012 | Smilde et al. |
| 2012/0242970 A1 | 9/2012 | Smilde et al. |
| 2013/0258310 A1 | 10/2013 | Smilde et al. |
| 2013/0271740 A1 | 10/2013 | Quintanilha |
| 2013/0278942 A1 | 10/2013 | Jeong et al. |
| 2017/0248852 A1 | 8/2017 | Warnaar et al. |

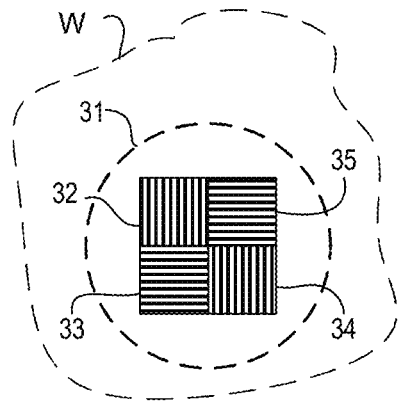 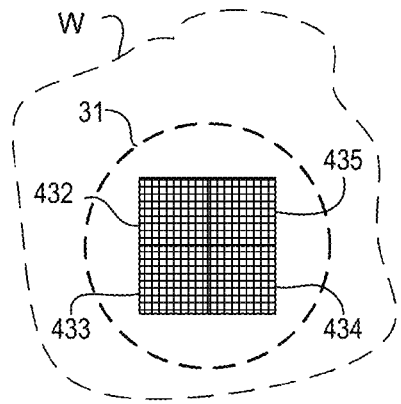
Fig. 4(a) (Prior art)  Fig. 4(b) (Prior art)
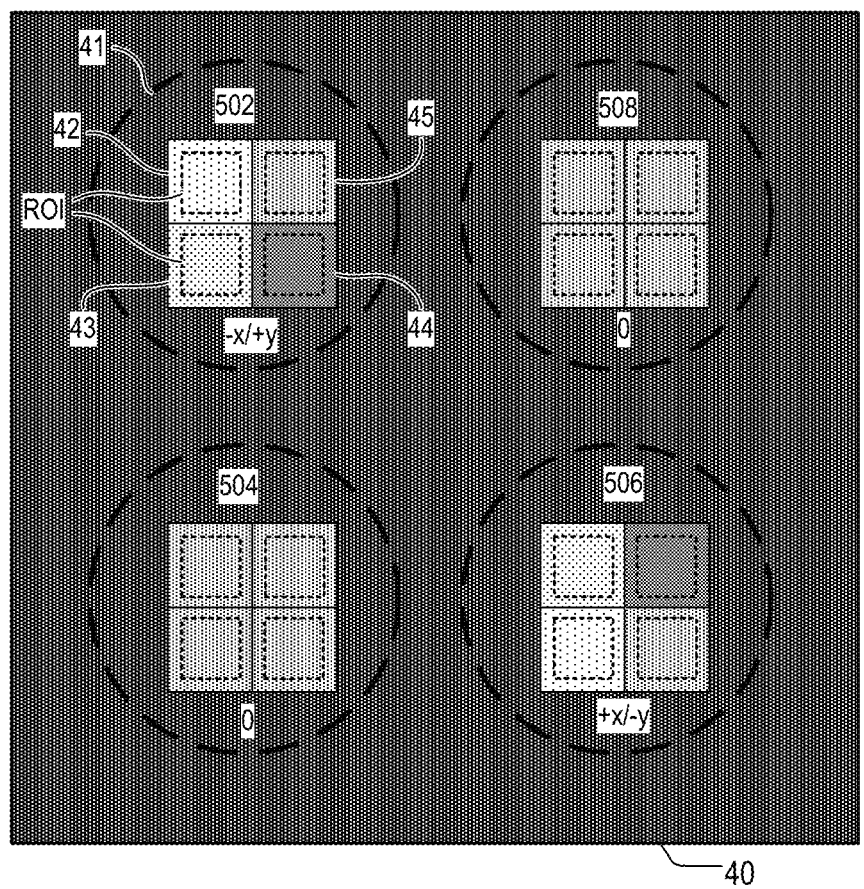
Fig. 5 (Prior art)

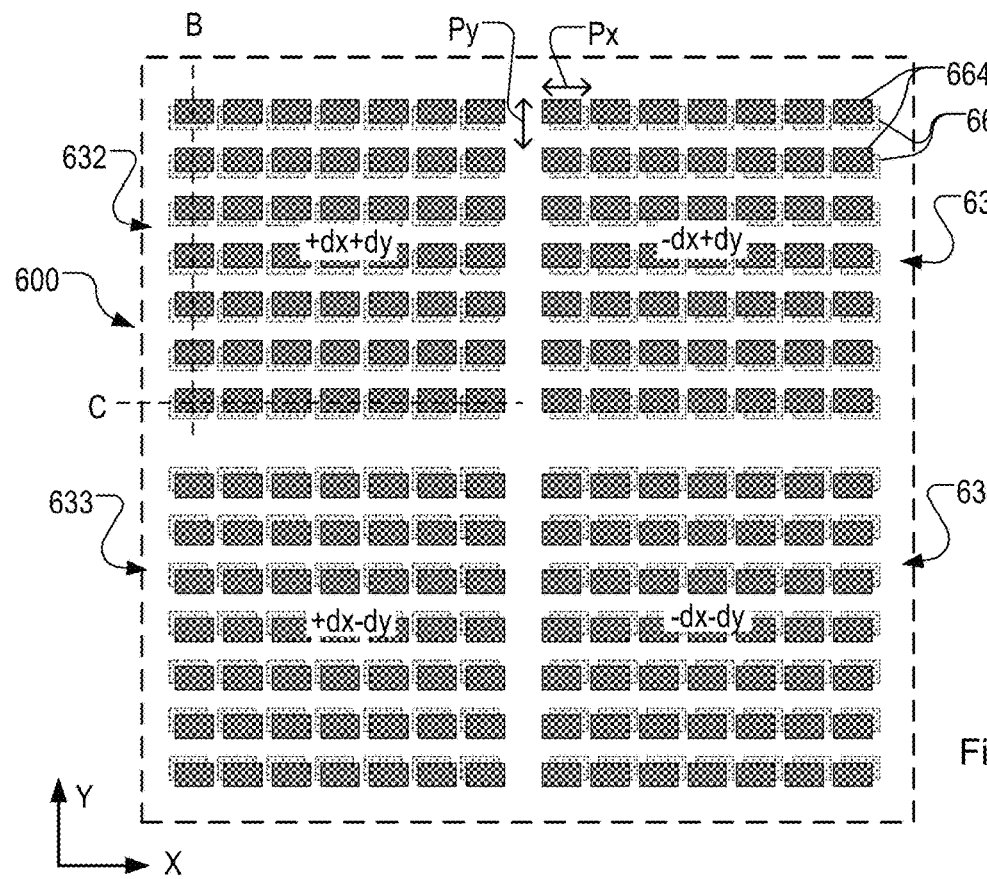
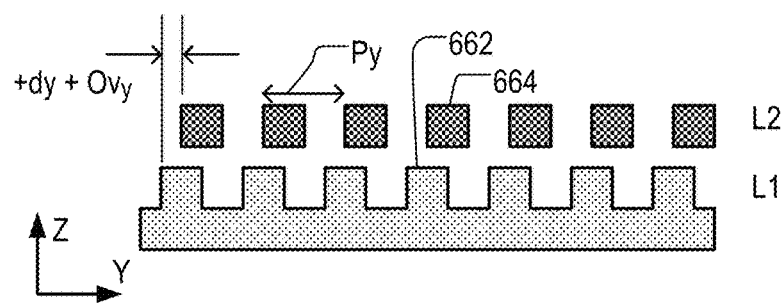
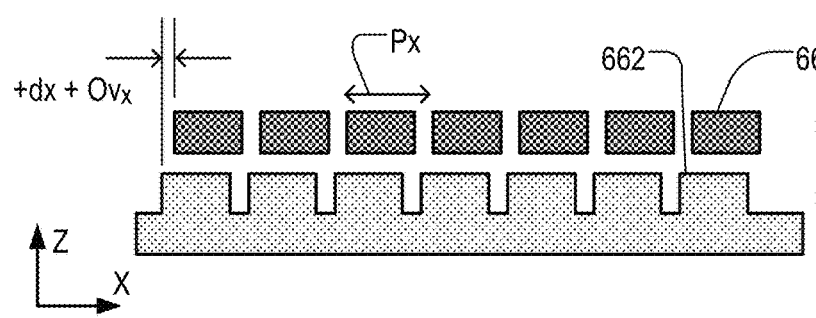

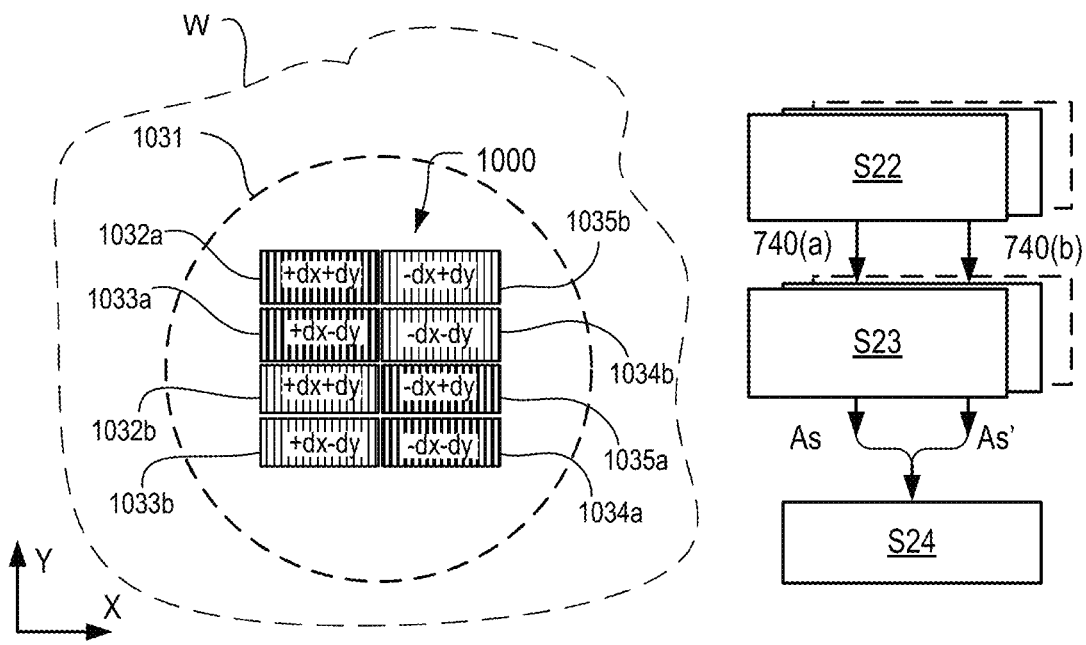
Fig. 10(a)
Fig. 10(b)
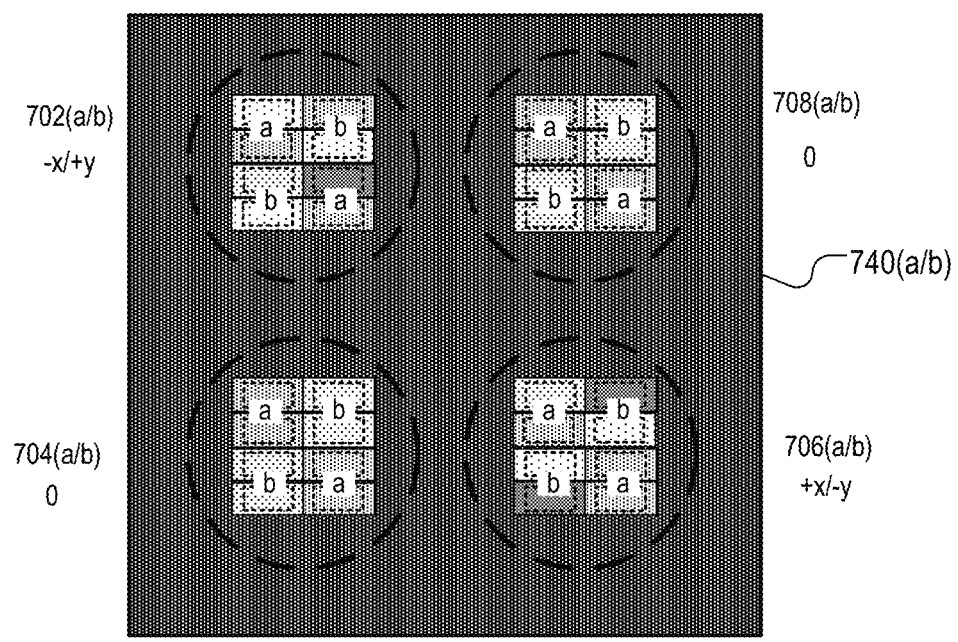
Fig. 11

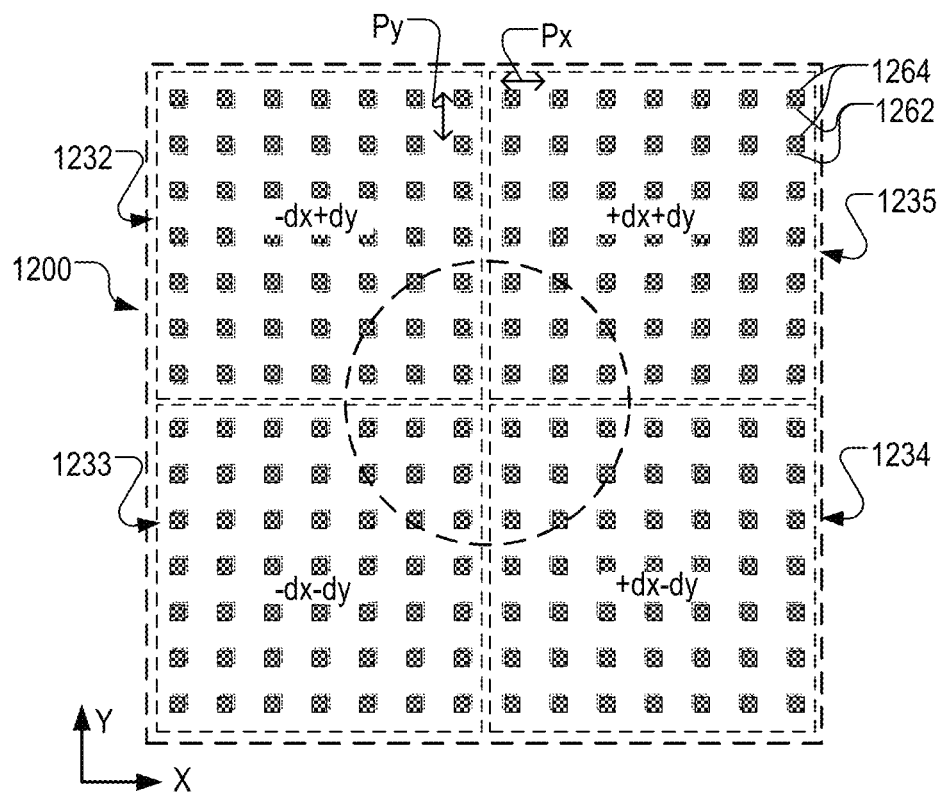
Fig. 12(a)
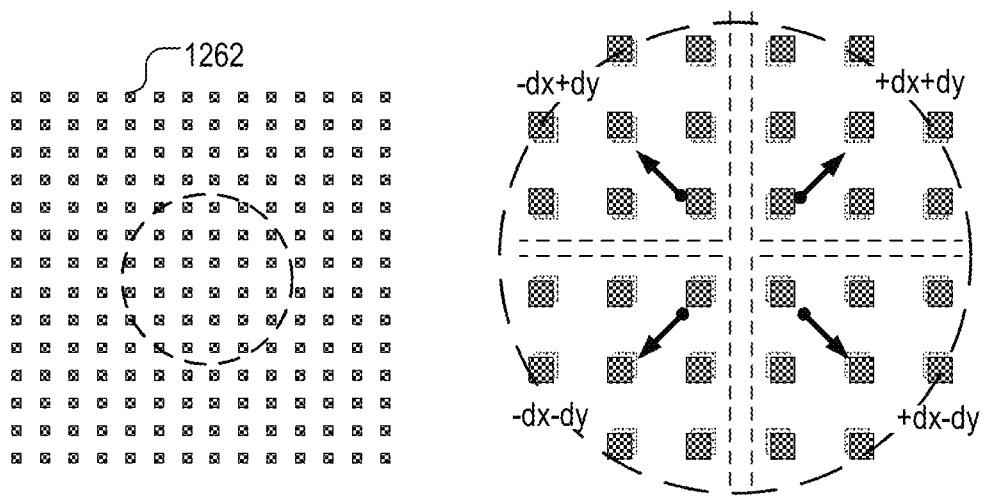
Fig. 12(b)
Fig. 12(c)

METHOD OF MEASURING A STRUCTURE, INSPECTION APPARATUS, LITHOGRAPHIC SYSTEM AND DEVICE MANUFACTURING METHOD

BACKGROUND

Field of the Invention

The present invention relates to methods and apparatus for metrology usable, for example, in the manufacture of devices by lithographic techniques, and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of a die, one die, or several dies) on a substrate (e.g., a silicon wafer). Transfer of the pattern is typically via imaging onto a layer of radiation-sensitive material (resist) provided on the substrate. In general, a single substrate will contain a network of adjacent target portions (known as fields) that are successively patterned.

In lithographic processes, it is desirable frequently to make measurements of the structures created, e.g. for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g. intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large gratings, e.g. 40 µm by 40 µm, and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables measurement of overlay and other parameters on smaller targets. These targets can be smaller than the illumination spot and may be surrounded by product structures on a substrate. The intensities from the environment product structures can efficiently be separated from the intensities from the overlay target with the dark-field detection in the image-plane.

Examples of dark field imaging metrology can be found in patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20120242970A1, US20130258310A, US20130271740A and WO2013178422A1. Typically, in these methods, it is desired to measure asymmetry as a property of the target. Targets can be designed so that measurement of asymmetry can be used to obtain measurement of various performance parameters such as overlay, focus or dose. Asymmetry of the target is measured by detecting differences in intensity between opposite portions of the diffraction spectrum using the scatterometer. For example, the intensities of +1 and −1 diffraction orders may be compared, to obtain a measure of asymmetry.

In order to reduce measurement time, known apparatuses for dark-field metrology have apertures and detection systems configured to detect simultaneously the radiation diffracted from component gratings in both X and Y directions, and to detect these different directions of diffraction independently. Thus, the need for separate detection steps in X and Y orientation is avoided. Examples of such techniques are included in the prior patent publications mentioned above, and also for example in unpublished patent application EP16157503.0.

There is often a desire for grating structures in metrology targets of the type described to be segmented in a direction other than their main direction of periodicity. Reasons for this segmentation may be to induce asymmetry-related effects to allow measurement of properties other than overlay by the same technique. Other reasons for this segmentation may be to make the grating structures more "product-like", so that they are printed with patterning performance more like the product structures that are primarily of interest. Grating structures may simply be completely two-dimensional in layout, for example to resemble an array of contact holes or pillars. Nevertheless, overlay or other parameters of the performance of the patterning process are normally controlled and measured separately in two or more directions, typically the X and Y directions defined relative to the substrate.

A particular problem arises when target structures have segmentation or other two-dimensional character in both sets of features (in both layers). Unfortunately, where the grating structures in a metrology target are two-dimensionally structured, either being fully two-dimensional gratings or having some kind of segmentation in the orthogonal to their main direction of periodicity, diffraction by a structure in the orthogonal direction becomes mixed with diffraction in the main direction, and the separate measurements become subject to noise or cross-talk. Moreover, in such targets, overlay error in two different directions will influence the diffraction signals captured by the inspection apparatus. The known methods tend to assume that each target structure has asymmetry only in a primary direction. When this assumption is no longer valid, known techniques inevitably become less accurate. To exacerbate this problem, in general it may not even be known to the operator of the metrology apparatus, whether metrology targets under investigation have two-dimensional properties of the type described.

SUMMARY OF THE INVENTION

The present invention in a first aspect aims to allow efficient measurement of a performance parameter such as overlay, even when target structures may be two-dimensional in nature. The present invention in another aspect aims to allow recognition of two-dimensional character in metrology targets, without relying on advance information.

The invention in a first aspect provides a method of determining overlay performance of a lithographic process, the method including the following steps:

(a) obtaining a plurality of target structures that have been formed by the lithographic process, each target structure comprising a set of first features arranged periodically in at least a first direction and a set of second features arranged periodically in at least the first direction and being subject to overlay error in the placement of the second features relative to the first features, (b) using a detection system to capture first diffraction signals comprising selected portions of radiation diffracted by at least a subset of the target structures;

(c) using the detection system to capture second diffraction signals comprising selected portions of radiation diffracted by at least a subset of the overlay targets;

(d) processing asymmetry information derived from the first diffraction signals and the second diffraction signals to calculate at least a measurement of said overlay error in at least the first direction, wherein said target structures have been formed with programmed offsets in the placement of the second features relative to the first features in addition to said overlay error, the programmed offsets within each subset differing in both the first direction and in a second direction, the first and second directions being non-parallel, and wherein the calculation of overlay error in step (d) combines said asymmetry information with knowledge of said programmed offsets while making no assumption whether asymmetry in a given target structure results from relative displacement of the second features in the first direction, in the second direction or both directions.

With a suitable bias scheme the method allows overlay and other asymmetry-related properties to be measured accurately, even in the presence of (potentially unknown) two-dimensional structure and unknown overlay in two directions. Additional sets of diffraction signals can be added, if desired, to enhance accuracy further.

In a first embodiment, the first and second diffraction signals are captured under different capture conditions. Capture conditions may differ for example in one wavelength, polarization, and/or angular distribution of radiation used for illumination and/or detection of the target structures.

In a second embodiment, first diffraction signals comprise radiation diffracted by a first subset of target structures and the second diffraction signals comprise radiation diffracted by a second subset of target structures, different from the first subset of target structures. The target structures of said first subset and the target structures of said second subset may for example differ in one or more of pitch, feature size, relative placement, and segmentation in the second direction.

In a third embodiment, the first and second subsets of target structures of similar design are printed in one step, with more than four different combinations of programmed offsets. Seven or eight different programmed offsets may be included in a composite metrology target.

The first, second and third embodiments can be combined, if desired.

The invention further provides an inspection apparatus for determining overlay performance of a lithographic process, the inspection apparatus comprising:

a support for a substrate on which are provided a plurality of target structures that have been formed by the lithographic process, each target structure comprising a set of first features arranged periodically in at least a first direction and a set of second features arranged periodically in at least the first direction and being subject to overlay error in the placement of the second features relative to the first features, an illumination system and a detection system which are together operable to capture first diffraction signals comprising selected portions of radiation diffracted by at least a subset of the target structures and second diffraction signals comprising selected portions of radiation diffracted by at least a subset of the overlay targets;

a processor for processing asymmetry information derived from the first diffraction signals and the second diffraction signals to calculate at least a measurement of said overlay error in at least the first direction, wherein said processor is operable on the basis that said target structures have been formed with programmed offsets in the placement of the second features relative to the first features in addition to said overlay error, the programmed offsets within each subset differing in both the first direction and in a second direction, the first and second directions being non-parallel, and said processor is arranged to calculate overlay error by combining said asymmetry information with knowledge of said programmed offsets while making no assumption whether asymmetry in a given target structure results from relative displacement of the second features in the first direction, in the second direction or both directions.

The inspection apparatus can be implemented applying optical systems and techniques known from the prior art, or using new apparatus. The inspection apparatus can be implemented for example using the above-mentioned dark-field imaging techniques, thereby obtaining the first and/or second diffraction signals for a plurality of target structures in a single image.

The invention in another aspect provides a metrology target for use in a method according to the first aspect of the invention as set forth above, wherein said metrology target includes at least four target structures, each target structure comprising first features periodic in both a first direction and a second direction and second features periodic in both the first direction and the second direction, the first and second directions being non-parallel, and wherein said target structures have programmed offsets in placement of the second features relative to the first features in both the first direction and the second direction, each target structure within said at least four target structures having a different combination of programmed offset in the first and second directions.

The invention in a further, independent aspect provides a metrology target for use in overlay metrology, said metrology target including a plurality of target structures, each target structure comprising first features periodic in both a first direction and a second direction and second features periodic in both the first direction and the second direction, the first and second directions being non-parallel, and wherein different ones of said target structures have different programmed offsets in placement of the second features relative to the first features in both the first direction and the second direction, and wherein said target structures are arranged into said metrology target such that any target structure bordering two neighboring target structures has a programmed offset intermediate between the programmed offsets of those two neighboring target structures.

The invention in a further aspect provides a set of patterning devices for use in a lithographic process, the patterning devices including at least a first patterning device configured to define the first features of a metrology target according to any aspect of the invention as set forth above, and a second patterning device configured for to define the second features of the metrology target.

The invention in another aspect provides a processing device arranged to receive at least first and second diffraction signals captured from a plurality of target structures and to derive a measurement of overlay error in at least a first direction by performing the step (d) in the method according to the first aspect of the invention as set forth above.

The invention further provides one or more computer program products comprising machine readable instructions for causing a programmable processing device to implement one or more aspects of the invention as set forth above. The machine readable instructions may be embodied, for example, in a non-transitory storage medium.

The machine readable instructions may be further arranged to cause the programmable processing device to control automatically the operation of an inspection apparatus to cause capture of the first and second diffraction signals by steps (b) and (c) of the method.

The invention further provides a lithographic system including a lithographic apparatus and an inspection apparatus according to the second aspect of the invention, as set forth above.

The invention further provides a method of manufacturing devices wherein a device pattern is applied to a series of substrates using a lithographic process, the method including measuring one or more performance parameters using a plurality of target structures formed as part of or beside said device pattern on at least one of said substrates using a method according to the invention as set forth above, and controlling the lithographic process for later substrates in accordance with the result of the measuring.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Figure 2A:
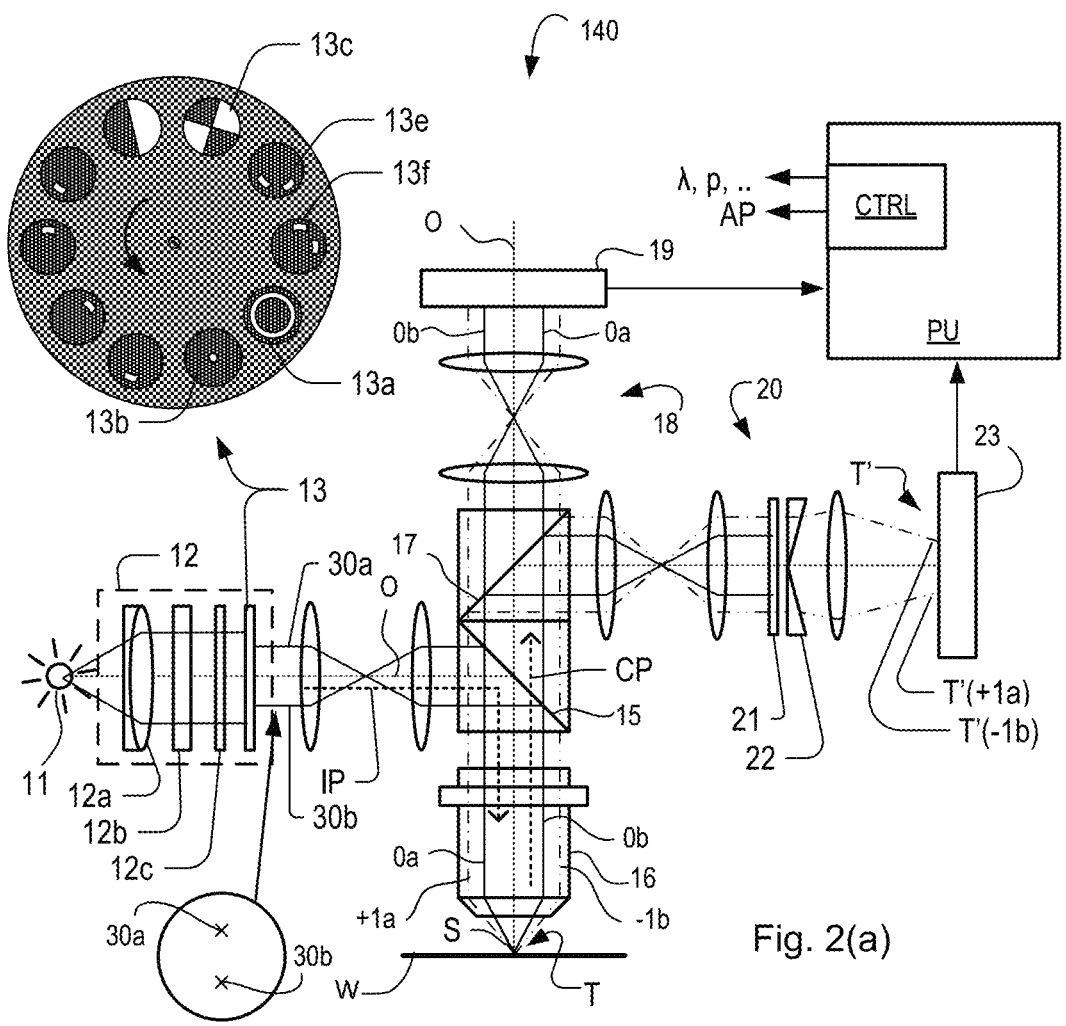
Figure 2B:
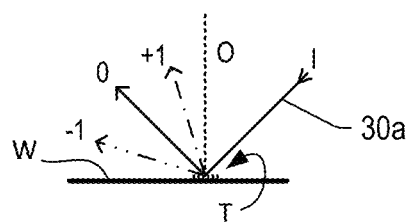
Figure 3A:
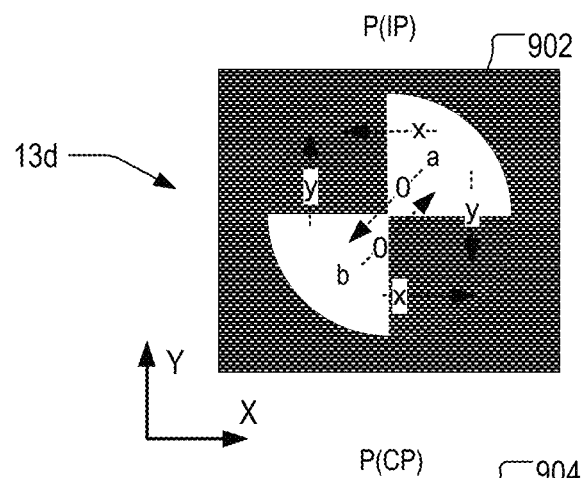
Figure 3B:
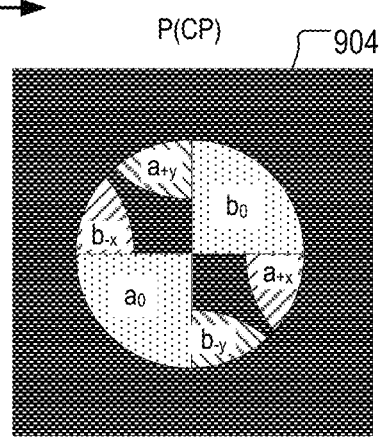
Figure 3C:
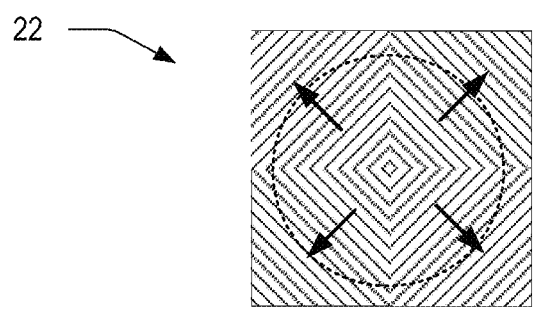
Figure 7:
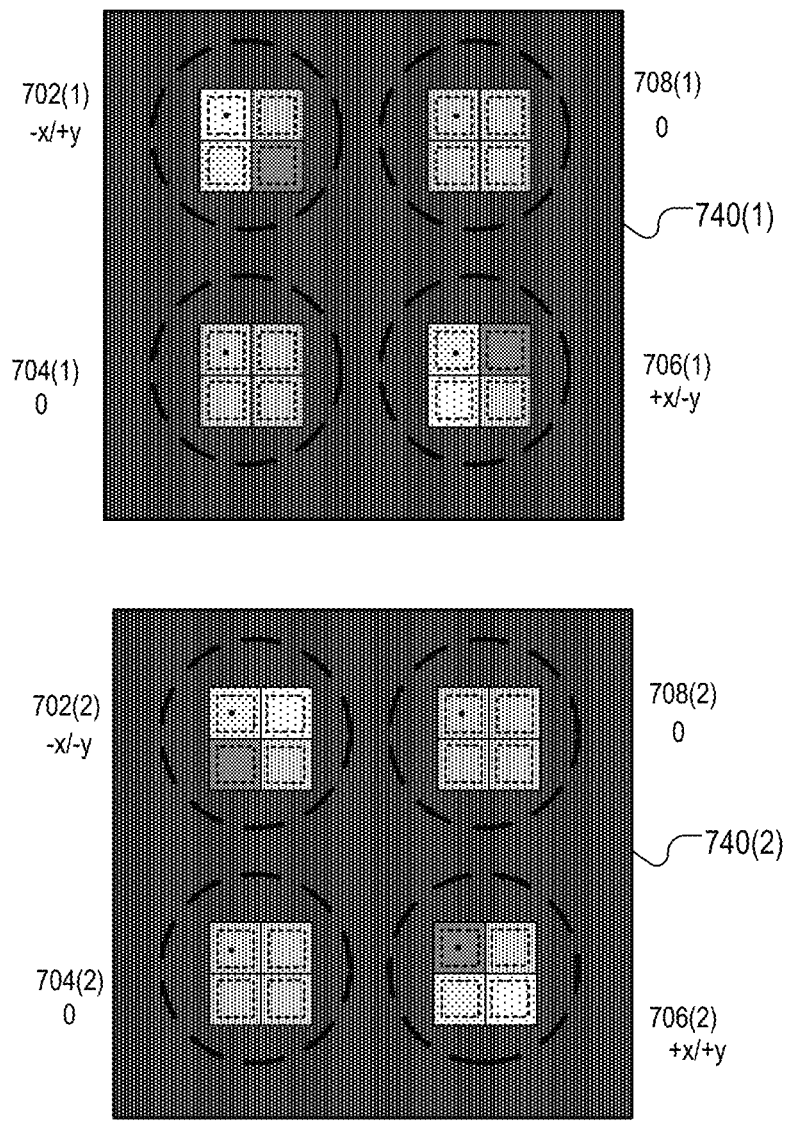
Figure 8:
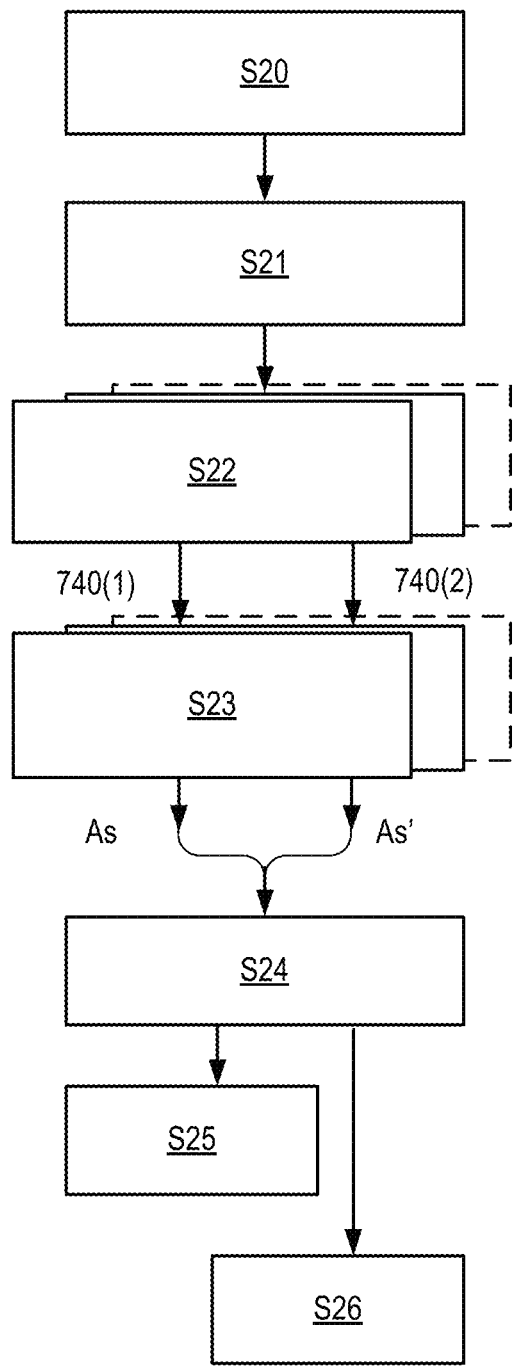
Figure 9A:
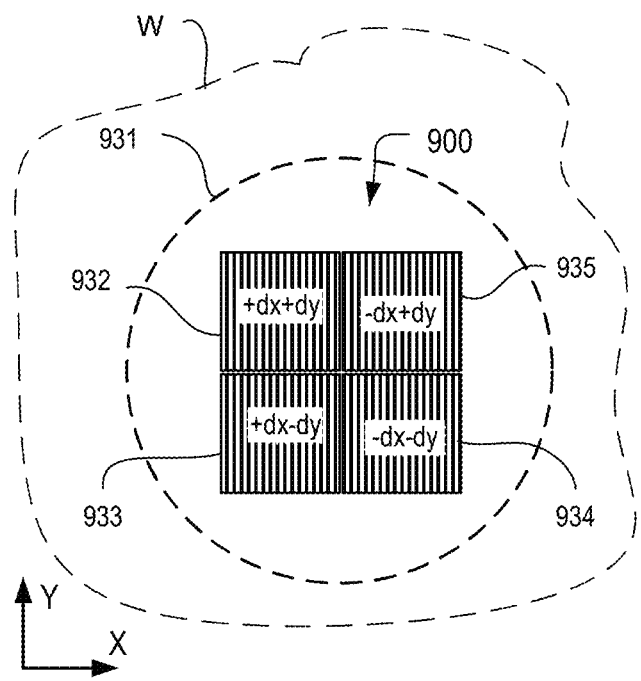
Figure 9B:
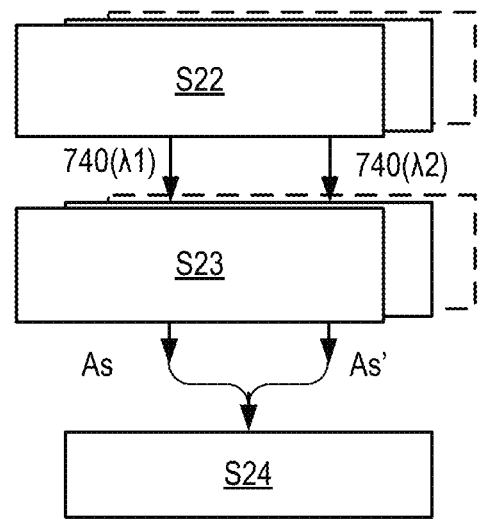
Figure 13:
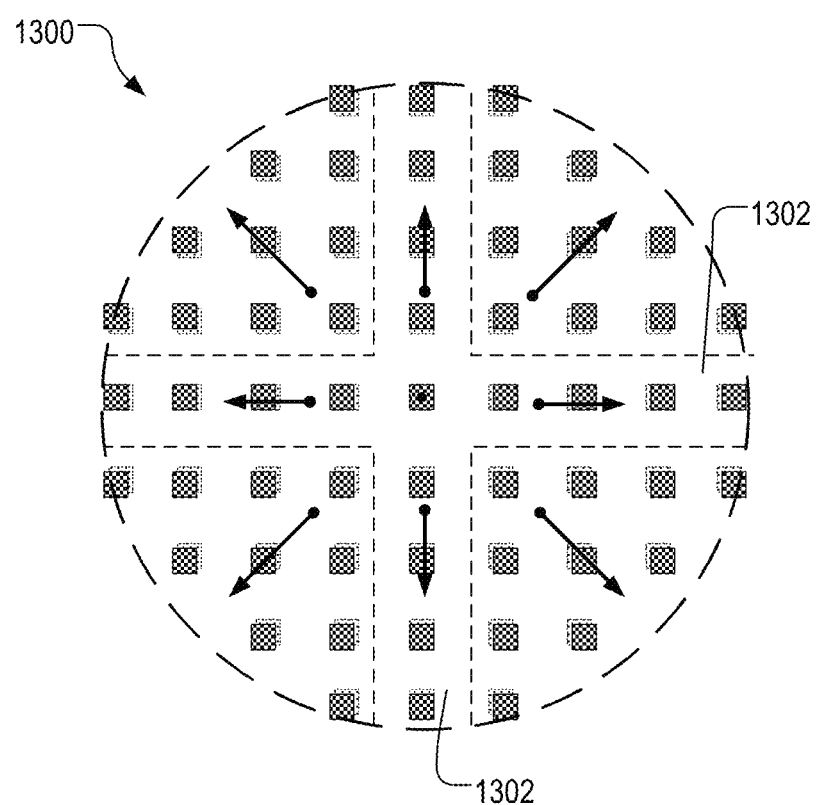
Figure 14A:
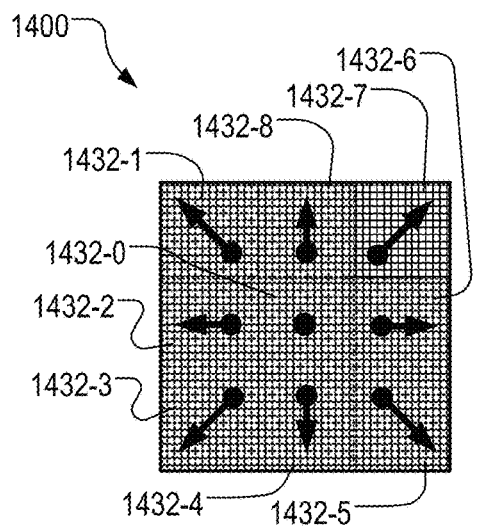
Figure 14B:
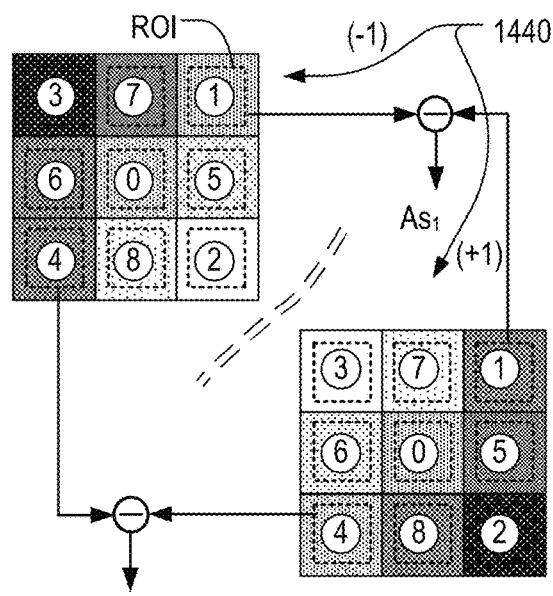
Figure 15:
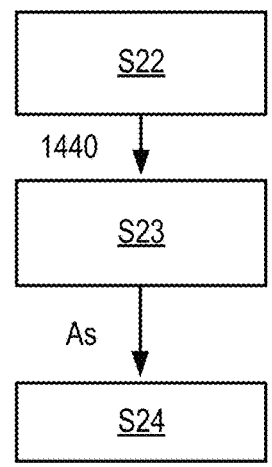
Figure 16A:
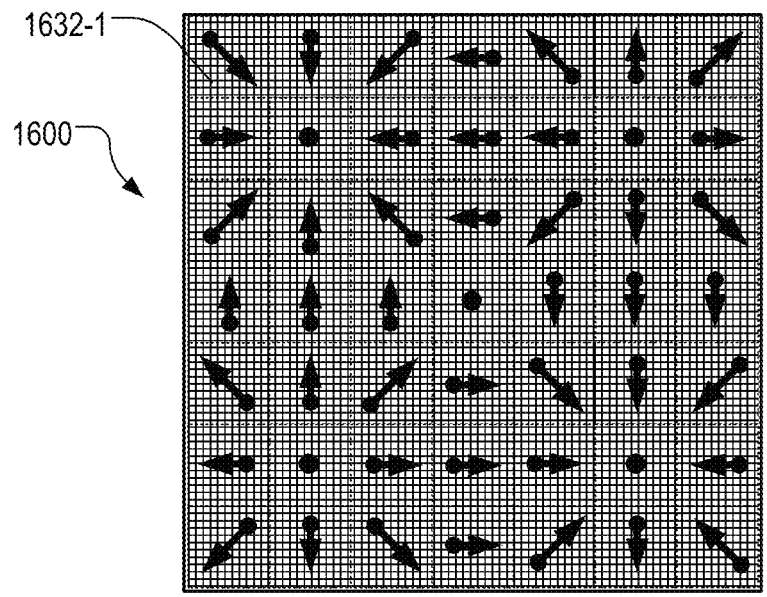
Figure 16B:
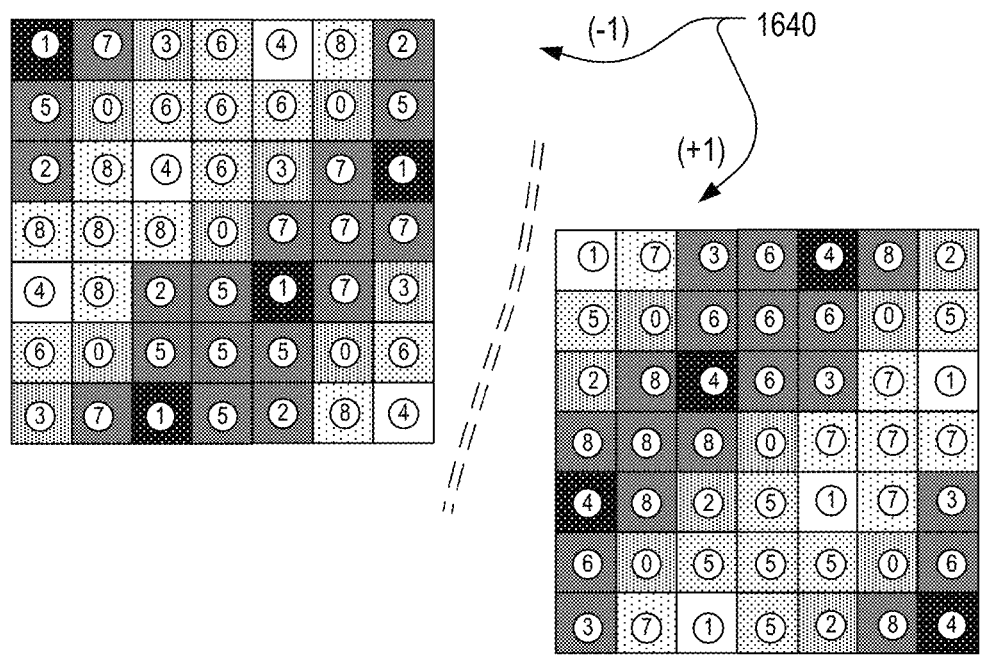
Figure 17A:
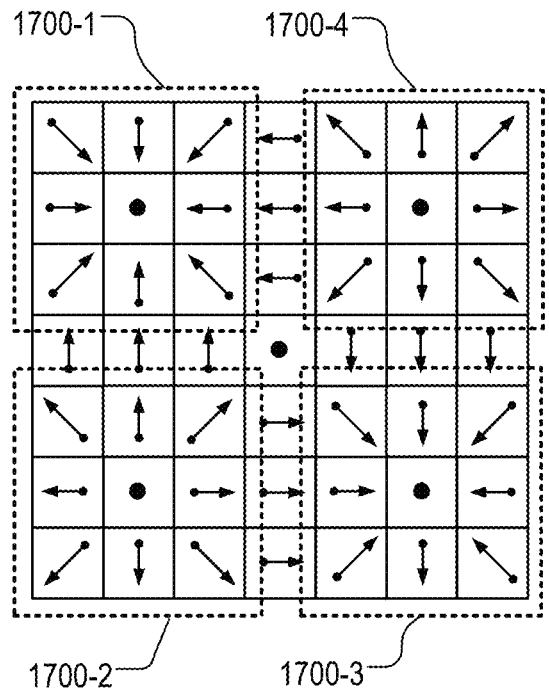
Figure 17B:
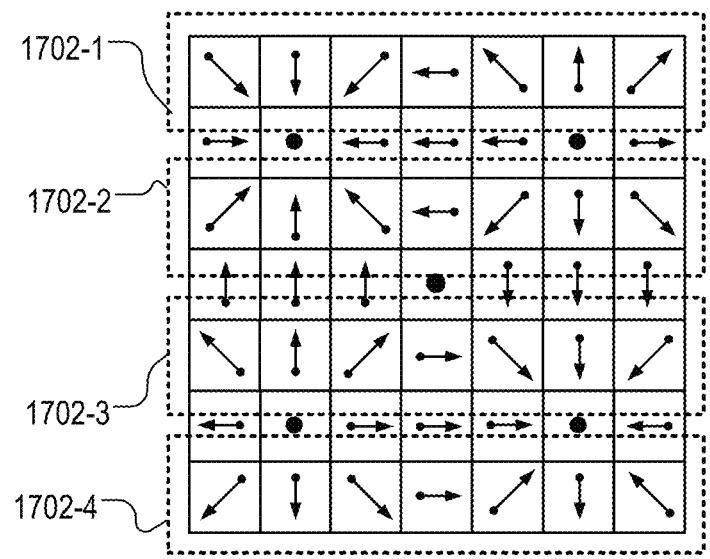

Embodiments of the invention will now be described, by way of example, with reference to the accompanying drawings in which:

FIG. 1 depicts a lithographic apparatus together with other apparatuses forming a production facility for semiconductor devices;

FIGS. 2(a)-2(b) illustrate schematically 2(a) an inspection apparatus adapted to perform angle-resolved scatterometry and dark-field imaging inspection methods in accordance with some embodiments of the invention and 2(b) an enlarged detail of the diffraction of incident radiation by a target grating in the apparatus of FIG. 2(a);

FIGS. 3(a)-3(c) illustrate 3(a) a segmented illumination profile, 3(b) the production of diffraction signals in different directions under the segmented illumination profile and 3(c) the layout of a prism device in a segmented detection system, all in the operation of one embodiment of the inspection apparatus of FIG. 2;

FIGS. 4(a)-4(b) illustrate a composite metrology target including a number of component gratings 4(a) in a case where each component grating is periodic in only one direction and 4(b) in a case where each component grating is or may be periodic in two directions;

FIG. 5 illustrates a multiple image of the target of FIG. 4, captured by the apparatus of FIG. 4 with spatial separation of diffraction orders;

FIGS. 6(a)-6(c) illustrate an example target layout according to a first embodiment of the present disclosure, in plan view and with cross-sections along lines B and C;

FIG. 7 illustrates dark-field images of the target of FIG. 6 obtained using first and second measurement conditions in a method according to the first embodiment of the present disclosure;

FIG. 8 is a flowchart of a method of measuring a property of a target structure and a method of controlling a lithographic process using the principles of the present disclosure; and FIGS. 9(a)-9(b) illustrates 9(a) a target layout similar to that of FIGS. 6 and 9(b) implementation of part of the method of FIG. 8 using such a target in accordance with the first embodiment of the present disclosure;

FIGS. 10(a)-10(b) illustrate 10(a) a target layout according to a second embodiment of the present disclosure and 10(b) implementation of part of the method of FIG. 8 using such a target in accordance with the second embodiment of the present disclosure;

FIG. 11 illustrates a dark-field image of the target of FIG. 6 obtained using first and second target types in a method according to the second embodiment of the present disclosure;

FIGS. 12(a)-12(c) illustrate 12(a) a metrology target according to a modified first embodiment of the present disclosure, 12(b) one set of features defined in the target layout and 12(c) detail of a central portion of the target layout circled in 12(a);

FIG. 13 illustrates a variant of the target of FIG. 12, including transition zones;

FIGS. 14(a)-14(b) illustrate 14(a) a metrology target according to a third embodiment of the present disclosure, and 14(b) part of a multiple image of the target, captured by the apparatus of FIG. 4 with spatial separation of diffraction orders, with a schematic representation of signal processing to obtain asymmetry signals from a plurality of target structures;

FIG. 15 illustrates implementation of part of the method of FIG. 8 using such a target in accordance with the third embodiment of the present disclosure;

FIGS. 16(a)-16(b) illustrate 16(a) an enlarged metrology target according to a modified third embodiment of the present disclosure, and 16(b) part of a multiple image of the target, captured by the apparatus of FIG. 4 with spatial separation of diffraction orders, with a schematic representation of signal processing to obtain asymmetry signals from a plurality of target structures; and FIGS. 17(a)-17(b) illustrate alternative groupings 17(a) and 17(b) of target structures in the embodiment of FIG. 16.

DETAILED DESCRIPTION OF EXEMPLARY EMBODIMENTS

Before describing embodiments of the invention in detail, it is instructive to present an example environment in which embodiments of the present invention may be implemented.

FIG. 1 at 100 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 100 for short), a measurement station MEA is shown at 102 and an exposure station EXP is shown at 104. A control unit LACU is shown at 106. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU controls the movements and measurements of various actuators and sensors, causing the apparatus LA to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA for example is of a so-called dual stage type which has two substrate tables WTa and WTb and two stations—an exposure station and a measurement station—between which the substrate tables can be exchanged.

Within the production facility, apparatus 100 forms part of a "litho cell" or "litho cluster" that contains also a coating apparatus 108 for applying photosensitive resist and other coatings to substrates W for patterning by the apparatus 100. At an output side of apparatus 100, a baking apparatus 110 and developing apparatus 112 are provided for developing the exposed pattern into a physical resist pattern. Between all of these apparatuses, substrate handling systems take care of supporting the substrates and transferring them from one piece of apparatus to the next. These apparatuses, which are often collectively referred to as the "track", are under the control of a track control unit which is itself controlled by a supervisory control system SCS, which also controls the lithographic apparatus via lithographic apparatus control unit LACU. Thus, the different apparatuses can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 120 are transferred to other processing apparatuses such as are illustrated at 122, 124, 126. A wide range of processing steps is implemented by various apparatuses in a typical manufacturing facility. For the sake of example, apparatus 122 in this embodiment is an etching station, and apparatus 124 performs a post-etch annealing step. Further physical and/or chemical processing steps are applied in further apparatuses, 126, etc. Numerous types of operation can be required to make a real device, such as deposition of material, modification of surface material characteristics (oxidation, doping, ion implantation etc.), chemical-mechanical polishing (CMP), and so forth. The apparatus 126 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 130 arriving at the litho cluster may be newly prepared substrates, or they may be substrates that have been processed previously in this cluster or in another apparatus entirely. Similarly, depending on the required processing, substrates 132 on leaving apparatus 126 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 126 used at each layer may be completely different in type. Further, even where the processing steps to be applied by the apparatus 126 are nominally the same, in a large facility, there may be several supposedly identical machines working in parallel to perform the step 126 on different substrates. Small differences in set-up, or faults between these machines can mean that they influence different substrates in different ways. Even steps that are relatively common to each layer, such as etching (apparatus 122) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system MET which receives some or all of the substrates W that have been processed in the litho cell. Metrology results are provided directly or indirectly to the supervisory control system (SCS) 138. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 140 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 120 prior to etching in the apparatus 122. Using metrology apparatus 140, it may be determined, for example, that important performance parameters such as overlay or critical dimension (CD) do not meet specified accuracy requirements in the developed resist. Prior to the etching step, the opportunity exists to strip the developed resist and reprocess the substrates 120 through the litho cluster. As is also well known, the metrology results 142 from the apparatus 140 can be used to maintain accurate performance of the patterning operations in the litho cluster, by supervisory control system SCS and/or control unit LACU 106 making small adjustments over time, thereby minimizing the risk of products being made out-of-specification, and requiring re-work. Of course, metrology apparatus 140 and/or other metrology apparatuses (not shown) can be applied to measure properties of the processed substrates 132, 134, and incoming substrates 130.

Example Inspection Apparatus

FIG. 2(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 2(b).

As described in the prior applications cited in the introduction, the dark-field-imaging apparatus of FIG. 2(a) may be part of a multi-purpose angle-resolved scatterometer that may be used instead of, or in addition to, a spectroscopic scatterometer. In this type of inspection apparatus, radiation emitted by a radiation source 11 is conditioned by an illumination system 12. For example, illumination system 12 may include a collimating lens system 12a, a color filter 12b, a polarizer 12c and an aperture device 13. The conditioned radiation follows an illumination path IP, in which it is reflected by partially reflecting surface 15 and focused into a spot S on substrate W via an objective lens 16. A metrology target T may be formed on substrate W. The objective lens 16 may be similar in form to a microscope objective lens, but has a high numerical aperture (NA), preferably at least 0.9 and more preferably at least 0.95. Immersion fluid can be used to obtain numerical apertures over 1 if desired.

The objective lens 16 in this example serves also to collect radiation that has been scattered by the target. Schematically, a collection path CP is shown for this returning radiation. The multi-purpose scatterometer may have two or more measurement branches in the collection path. The illustrated example has a pupil imaging branch comprising pupil imaging optical system 18 and pupil image sensor 19. An imaging branch is also shown, which will be described in more detail below. Additionally, further optical systems and branches will be included in a practical apparatus, for example to collect reference radiation for intensity normalization, for coarse imaging of capture targets, for focusing and so forth. Details of these can be found in the prior publications mentioned above.

Where a metrology target T is provided on substrate W, this may be a 1-D grating, which is printed such that, after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus. In the case of gratings, the structure is periodic. In the case of an overlay metrology target, the grating is printed on top of or interleaved with another grating that has been formed by a previous patterning step.

The various components of illumination system 12 can be adjustable to implement different metrology 'recipes' within the same apparatus. In addition to selecting wavelength (color) and polarization as characteristics of the illuminating radiation, illumination system 12 can be adjusted to implement different illumination profiles. The plane of aperture device 13 is conjugate with a pupil plane of objective lens 16 and with the plane of the pupil image detector 19. Therefore, an illumination profile defined by aperture device 13 defines the angular distribution of light incident on substrate W in spot S. To implement different illumination profiles, an aperture device 13 can be provided in the illumination path. The aperture device may comprise different apertures 13a, 13b, 13c etc. mounted on a movable slide or wheel. It may alternatively comprise a fixed or programmable spatial light modulator (SLM). As a further alternative, optical fibers may be disposed at different locations in the illumination pupil plane and used selectively to deliver light or not deliver light at their respective locations. These variants are all discussed and exemplified in the documents cited above. The aperture device may be of a reflective form, rather than transmissive. For example, a reflective SLM might be used. Indeed, in an inspection apparatus working in the UV or EUV waveband most or all of the optical elements may be reflective.

Depending on the illumination mode, example rays 30a may be provided so that the angle of incidence is as shown at '1' in FIG. 2(b). The path of the zero order ray reflected by target T is labeled '0' (not to be confused with optical axis 'O'). Similarly, in the same illumination mode or in a second illumination mode, rays 30b can be provided, in which case the angles of incidence and reflection will be swapped compared with the first mode. In FIG. 2(a), the zero order rays of the first and second example illumination modes are labeled 0a and 0b respectively.

As shown in more detail in FIG. 2(b), target grating T as an example of a target structure is placed with substrate W normal to the optical axis O of objective lens 16. In the case of an off-axis illumination profile, a ray 30a of illumination I, impinging on grating T from an angle off the axis O, gives rise to a zeroth order ray (solid line 0) and two first order rays (dot-chain line +1 and double dot-chain line -1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/-1 will be spread out somewhat. According to the point spread function of a small target, the diffracted radiation of each order +1 and -1 will be further spread over a range of angles, not a single ideal ray as shown.

If the target has multiple periodic components, then each of those will give rise to first and higher diffracted rays, which may be in directions into or out of the page. The example of FIG. 2(b) is merely describing a one-dimensional grating for simplicity.

In the branch of the collection path for dark-field imaging, imaging optical system 20 forms an image T' of the target on the substrate W on sensor 23 (e.g. a CCD or CMOS sensor). An aperture stop 21 is provided in a plane in the imaging branch of the collection path CP which is conjugate to a pupil plane of objective lens 16. Aperture stop 21 may also be called a pupil stop. Aperture stop 21 can take different forms, just as the illumination aperture can take different forms. The aperture stop 21, in combination with the effective aperture of lens 16, determines what portion of the scattered radiation is used to produce the image on sensor 23. Typically, aperture stop 21 functions to block the zeroth order diffracted beam so that the image of the target formed on sensor 23 is formed only from the first order beam(s). In an example where both first order beams were combined to form an image, this would be the so-called dark field image, equivalent to dark-field microscopy.

The images captured by sensor 23 are output to image processor and controller PU, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose. Special designs of targets are provided to allow these measurements of different performance parameters to be made through the same basic asymmetry measurement method.

Processor and controller PU also generates control signals such as λ and AP, for controlling the illumination characteristics (polarization, wavelength) and for selecting the aperture using aperture device 13 or a programmable spatial light modulator. Aperture stop 21 may also be controlled in the same way. Each combination of these parameters of the illumination and the detection is considered a "recipe" for the measurements to be made.

Referring again to FIG. 2(b) and the illuminating rays 30a, +1 order diffracted rays from the target grating will enter the objective lens 16 and contribute to the image recorded at sensor 23. Rays 30b are incident at an angle opposite to rays 30a, and so the -1 order diffracted rays enter the objective and contribute to the image. Aperture stop 21 blocks the zeroth order radiation when using off-axis illumination. As described in the prior publications, illumination modes can be defined with off-axis illumination in X and Y directions.

Apertures 13c, 13e and 13f in the aperture device 13 of FIG. 2(a) include off-axis illumination in both X and Y directions, and are of particular interest for the present disclosure. Aperture 13c creates what may be referred to as a segmented illumination profile, and may for example be used in combination with a segmented aperture defined for example by a segmented prism 22, described below. Apertures 13e and 13f may for example be used in combination with an on-axis aperture stop 21, in a manner described in some the prior published patent applications, mentioned above.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture stop 21 could be used to pass substantially only one first order of diffracted light to the sensor. In a further example, a segmented prism 22 is used in combination with an on-axis illumination mode. The segmented prism 22 can be regarded as a combination of individual off-axis prisms, and can be implemented as a set of prisms mounted together, if desired. These prisms define a segmented aperture in which rays in each quadrant are deflected slightly through an angle. This deflection in the pupil plane in has the effect of spatially separating the +1 and -1 orders in each direction in the image plane. In other words, the radiation of each diffraction order and direction forms an image to different locations on sensor 23 so that they can be detected and compared without the need for two sequential image capture steps. Effectively, separate images are formed at separated locations on the image sensor 23. In FIG. 2(a) for example, an image T'(+1a), made using +1 order diffraction from illuminating ray 30a, is spatially separated from an image T'(−1b) made using −1 order diffraction from illuminating ray 30b. This technique is disclosed in the above-mentioned published patent application US20110102753A1, the contents of which are hereby incorporated by reference in its entirety. 2nd, 3rd and higher order beams (not shown in FIG. 2) can be used in measurements, instead of, or in addition to, the first order beams. As a further variation, the off-axis illumination mode can be kept constant, while the target itself is rotated 180 degrees beneath objective lens 16 to capture images using the opposite diffraction orders.

Whichever of these techniques is used, the present disclosure applies to methods in which radiation diffracted in two directions, for example the orthogonal directions called X and Y, is simultaneously captured.

While a conventional lens-based imaging system is illustrated, the techniques disclosed herein can be applied equally with plenoptic cameras, and also with so-called "lensless" or "digital" imaging systems. There is therefore a large degree of design choice, which parts of the processing system for the diffracted radiation are implemented in the optical domain and which are implemented in the electronic and software domains.

Image-based Asymmetry Measurement

Referring to FIG. 3 (a), and viewing the pupil plane of the illumination system P(IP) in the vicinity of aperture device 13, aperture 13c has been selected to define a specific spatial profile of illumination, illustrated at 902. In this desired spatial profile of the illumination system, two diametrically opposite quadrants, labeled a and b, are bright, while the other two quadrants are dark (opaque). This spatial illumination profile, when focused to form spot S on the target T, defines a corresponding angular distribution of illumination, in which rays from angles only in these two quadrants. This segmented type of aperture is known in scatterometry apparatus, from the published patent application US 2010/201963. The merits of this modified illumination aperture will be described further below.

When rays from the bright segments of the illumination profile 902 are diffracted by periodic features in a target structure, they will be at angles corresponding to a shift in the pupil plane. Arrows 'x' in FIG. 3 (a) indicate the direction of diffraction of illumination caused by structures periodic in the X direction, while arrows 'y' indicate the direction of diffraction of illumination caused by structures periodic in the Y direction. Arrows '0' indicate direct reflection, in other words zero order diffraction. A feature of this segmented type of aperture is that, with regard to lines of symmetry defined by expected directions of diffraction (X and Y in this example), illuminated regions of the illumination profile are symmetrically opposite dark regions. Therefore there is the possibility to segregate the higher order diffracted radiation, while collecting radiation directed in both directions simultaneously.

FIG. 3 (b) illustrates a distribution of illumination in a conjugate pupil plane P(CP) in the collection path of the inspection apparatus. Assume firstly that the target T is a one-dimensional diffraction grating, with a periodicity in the X direction as a first direction. While the spatial profile 902 of the illumination has bright quadrants labeled a and b, the diffraction pattern resulting from diffraction by the lines of the target grating is represented by the pattern at 904 in FIG. 3 (b). In this pattern, in addition to zero order reflections labeled $a_0$ and $b_0$ there are first order diffraction signals visible, labeled $a_{+x}$, $b_{-x}$. Because other quadrants of the illumination aperture are dark, and more generally because the illumination pattern has 180° rotational symmetry, the diffraction orders $a_{+x}$ and $b_{-x}$ are "free", meaning that they do not overlap with the zero order or higher order signals from other parts of the illumination aperture (considering only the X direction at this stage). This property of the segmented illumination pattern can be exploited to obtain clear first order signals from a diffraction grating (alignment mark) having a pitch which is half the minimum pitch that could be imaged if a conventional, circularly-symmetric illumination aperture were used.

Now, assume that the target has periodic features in a second direction, for example the Y direction which is orthogonal to the first direction. These features in the second direction may arise from segmentation in the nominally one-dimensional grating. They may also arise from other one-dimensional gratings with Y orientation, that may be present within the area of spot S and the within the field of view of the inspection apparatus. They may also arise from a mixture of these. Assume further that the features periodic in the Y direction have the same period, and therefore the same diffraction angle, as the features periodic in the X direction. The result is diffraction signals $a_{+y}$ and $b_{-y}$ that can be seen in the pupil 904 of the collection path. These signals comprise first order diffraction signals in the Y direction. For simplicity of illustration in the present drawings, the diffraction signals in the Y direction and the X direction are shown as free of one another. In practice, the X diffraction signals and the Y diffraction may overlap in the pupil 904. The reader skilled in the art will understand that this depends on the pitches of the target in X and Y and the chosen wavelength.

Zero order signals $a_0$ and $b_0$ are also present in the pupil of the collection system, as illustrated. Depending whether these zero order signals are wanted or not, they may be blocked by a segmented aperture stop 21, similar in form to aperture 13d. For asymmetry-based measurements, it is generally the higher order signals, for example the +1 and −1 order signals that are of interest.

In the simple example illustrated, the Y direction diffraction signals do not overlap the X direction diffraction signals in the pupil of the collection path, but in other situations they might overlap, depending on the pitch of the grating and the wavelength of illumination. In any case, where two-dimensional features of some kind are present, diffraction signals from two directions can become mixed in the same quadrants of the pupil in the collection path. In the case of segmented gratings, the segmentation in one or both directions may be much finer than the pitch of the grating in the other direction. Where very fine segmentation is present, the higher order diffraction signals may fall completely outside the aperture of the collection path, but the present inventors have recognized that the diffraction in the second direction may nevertheless cause a change in the signals from the first direction, which do fall into the quadrants at top left and bottom right in FIG. 3(b).

FIG. 3 (c) shows schematically the layout of the segmented prism 22 in the imaging branch of the inspection apparatus of FIG. 2. The circular pupil P(CP) is represented by a dotted circle. In each quadrant of the pupil, a differently angled prism is provided, which deflects the radiation through a certain angle. This angular deflection in the pupil plane translates into a spatial separation of images in the plane of the detector 23, as illustrated already above with reference to FIG. 2(a). The operation of the apparatus in this type of configuration, and some practical benefits and challenges, will now be described in further. The principles of the present disclosure are applicable in other configurations, however.

FIG. 4 depicts a composite metrology target formed on a substrate W according to known practice. The composite target comprises four target structures in the form of gratings 32 to 35 positioned closely together so that they will all be within the measurement spot S formed by the illumination beam of the metrology apparatus. A circle 31 indicates the extent of spot S on the substrate W. The four target structures thus are all simultaneously illuminated and simultaneously imaged on sensor 23. In an example dedicated to overlay measurement, gratings 32 to 35 are themselves overlay gratings formed by first features and second features that are patterned in different lithographic steps. For ease of description it will be assumed that the first features and second features are formed in different layers of the semiconductor device formed on substrate W, but they may alternatively be formed in one layer, for example as part of a multiple patterning process. Gratings 32 to 35 may be differently biased, meaning that they have designed-in overlay offsets additional to any unknown overlay error introduced by the patterning process. Knowledge of the biases facilitates measurement of overlay between the layers in which the different parts of the overlay gratings are formed. Gratings 32 to 35 may also differ in their orientation, as shown, so as to diffract incoming radiation in X and Y directions.

In one known example, gratings 32 and 34 are X-direction gratings with biases of +d, −d, respectively in the placement of one grating relative to another. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. Separate images of these gratings can be identified in the image captured by sensor 23. While four gratings are illustrated, another embodiment might require a larger matrix to obtain the desired accuracy.

FIG. 5 shows an example of an image that may be formed on and detected by the sensor 23, using the target of FIG. 4 in the apparatus of FIGS. 2-3, using the segmented illumination profile and using the segmented prisms 22. Such a configuration provides off-axis illumination in both X and Y orientations simultaneously, and permits detection of diffraction orders in X and Y simultaneously, from the quadrants at upper left and lower right of the pupil 904 in FIG. 3(b).

The dark rectangle 40 represents the field of the image on the sensor, within which the illuminated spot 31 on the substrate is imaged into four corresponding circular areas, each using radiation only from one quadrant of the pupil 904 in the collection path CP. Four images of the target are labelled 502 to 508. Within image 502 the image of the illuminated spot 31 using radiation of the upper left quadrant of the pupil 904 is labelled 41. Within this, rectangular areas 42-45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole.

As mentioned and as illustrated in FIG. 5, because of the action of the segmented prism 22 on the signals in the pupil 904 of the collection path, and because of the segmented illumination profile 902 and its orientation relative to the X and Y directions of the target T, each of the four images 502-508 uses only certain portions of the diffraction spectra of each target. Thus the images 504 and 508 at lower left and upper right respectively are formed of the zero order radiation $a_0$ and $b_0$ respectively. The image 502 is formed of higher order diffracted radiation, specifically radiation diffracted in the negative X direction from bright quadrant b and the positive Y direction from bright quadrant a (diffraction signals $a_{+y}$ and $b_{-x}$). Conversely, image 506 is formed of higher order diffracted radiation, specifically radiation diffracted in the positive X direction from bright quadrant b and the negative Y direction from bright quadrant a (diffraction signals $a_{-y}$ and $b_{+x}$).

From the target comprising only one-dimensional gratings, there is no cross-talk between signals diffracted in the X direction and signals diffracted in the Y direction. That is because each component grating 31-35 diffracts radiation in only one of the two directions, and the image of each grating is spatially separated within the images 502-508 by the imaging action of the optical system. Once the separate images of the gratings have been identified, the intensities of those individual images can be measured, e.g., by averaging or summing selected pixel intensity values within the identified areas (ROIs). Intensities and/or other properties of the images can be compared with one another to obtain measurements of asymmetry for the four or more gratings simultaneously. These results can be combined with knowledge of the target structures and bias schemes, to measure different parameters of the lithographic process. Overlay performance is an important example of such a parameter, and is a measure of the lateral alignment of two lithographic layers. Overlay can be defined more specifically, for example, as the lateral position difference between the center of the top of a bottom grating and the center of the bottom of a corresponding top-grating. To obtain measurements of other parameters of the lithographic process, different target designs can be used. Again, knowledge of the target designs and bias schemes can be combined with asymmetry measurements to obtain measurements of the desired performance parameter. Target designs are known, for example, for obtaining measurements of dose or focus from asymmetry measurements obtained in this way.

Problems with Two-Dimensional Targets

Referring now to FIG. 4 (b), as mentioned above, some targets will scatter or diffract radiation in two directions within the same part of the image. The target of FIG. 4 (b) has two-dimensional structures in each of the four component gratings 432-435. The two dimensional structures may arise from segmentation in a one-dimensional grating in one or more layers. The two-dimensional structures may alternatively arise from gratings representing arrays of contact holes or vias, for example, which are fully 2-dimensional.

Although diffraction will therefore occur in both directions X and Y, within each grating image 42-45, nevertheless the purpose of the metrology target is to measure a parameter such as overlay separately in one or both of the X and Y directions. The contribution of diffraction from the other direction, in the same part of the image, represents "contamination" or noise in the wanted diffraction signals. In the overlay measurement we derive X-overlay from the asymmetry (difference between +1st and −1st order diffraction) in the X direction. Even at a simplistic level, it can be appreciated that the added radiation from diffraction in the Y direction leads to a worse signal to noise ratio. If the segmentation is present in both layers (or has an asymmetric shape), the added diffraction will not just add light, but also add asymmetry. Moreover since overlay error may arise in both directions, variations in asymmetry signals assumed to relate to one direction may be sensitivity to overlay errors in the other direction. This problem arises regardless whether the diffraction signals in the second direction fall within the detection pupil 904. This will lead to measurement errors, on top of the signal to noise degradation.

Overlay Targets for Two-Dimensional Overlay Measurement

FIG. 6 shows enlarged schematic views (a), (b) and (c) of a metrology target 600 formed on a substrate and adapted for overlay measurement in accordance with a first embodiment of the present disclosure. The metrology target in this example comprises four target structures 632, 633, 634, 635 which may have a size and layout similar to the gratings 32-35 in the target of FIG. 4(a). The view (a) is a plan view from above the substrate. The view (b) is a cross-section along the line B in view (a) and the view (c) is a cross-section along the line C. As can be seen, each target structure 632-635 includes a set of first features 662 arranged periodically in at least a first direction. The first direction is the Y direction in this example, and each first feature 662 comprises a bar which is segmented in the second (X) direction. A period Px of segmentation and a duty cycle of segmentation in the second direction are different to a period Py and duty cycle in the first direction, though they could be the same in another example.

Each target structure 632-635 further includes a set of second features 664 arranged periodically in at least the first direction. The second features 664 in this example are also bars segmented in the second direction, with the same period Py in the first direction and the same period Px of segmentation in the second direction. As shown in the cross-sectional views (b) and (c) the first features in this example are formed in a first layer L1 of the target structure and the second features are formed in a second layer L2. In other examples, formed for example by multiple patterning processes, the first features and second features might be formed in a single layer.

Overlay performance relates to the ability of a lithographic manufacturing process to place second features precisely, relative to the positions of existing first features. Suppose that the target design is such that nominally each second feature is placed exactly on top of a corresponding first feature. In the presence of overlay error, the second features become displaced by an amount OVx in the X direction and OVy in the Y direction, relative to their corresponding first features. It is assumed that the overlay error in both directions is constant over the small area of metrology target 600, though it may vary between metrology targets across a substrate and between substrates. The overlay error may result from inaccurate placement of the second features themselves, or it may result from distortion of the first features, caused for example in the patterning step by which the first features were formed, or in subsequent chemical and/or physical processing steps.

As is known, target structures for overlay metrology can be formed with programmed offsets (also known as "bias"), in addition to the (unknown) overlay error. These bias values are programmed into the target structures by appropriate design of the patterning devices MA that are used to define the first features and second features in the different layers L1 and L2 of the substrate. In the known target of FIG. 4(a) each target structure has bias in only one direction for measurement of overlay in that direction. It is assumed that overlay error in the other direction does not influence the measurement, but that turns out not to be the case. The inventors have recognized that, even in cases where diffraction orders in the second direction do not fall within the pupil of the detection system, target structures that are two-dimensional in both sets of features suffer from crosstalk between overlay in the first direction and overlay in the second direction. The inventors have further recognized that a bias scheme that includes appropriate combinations of bias values in both the first direction and the second direction can be used to obtain overlay measurements in the first direction that are corrected for the effects of periodic features and overlay variations in the second direction.

In the example target 600, with respect to the first direction (Y), positive bias values +dy are programmed into the target structures 632 and 635, displacing the second features upward in FIG. 6(a), while negative bias values −dy are programmed into the target structures 633 and 634. With respect to the second direction (X), positive bias values +dx are programmed into the target structures 632 and 633, displacing the second features to the right in FIG. 6(a), while negative bias values −dx are programmed into the target structures 634 and 635. As illustrated in the views (b) and (c), the actual placement of the second features relative to the first features is a combination of the programmed bias value in each direction and the unknown overlay error in that direction.

Thus the metrology target illustrated in FIG. 6 includes target structures with four different combinations of bias in the two directions of periodicity. The target in this example clearly has the Y direction as its primary direction, and segmentation in the X direction will cause weaker diffraction. This target is therefore designed primarily to measure overlay in the Y direction. A similar metrology target can be provided, if desired, arranged so that the primary direction of periodicity is the X direction, allowing measurement of overlay more accurately in the X direction. A target in which periodic effects are equally strong in both directions could be used to measure overlay equally accurately in both directions.

Mathematical Model

Now let us consider how the intensities of the individual grating areas within the image are conventionally used to calculate (one-dimensional) overlay error Ov from a pair of (one-dimensional) biased gratings (FIG. 4(a)). In a simplified linear approximation, the overlay OV is calculated by using the intensities from the individual target structures (gratings 32-35):

$$Ov = d\left(\frac{(I_{+d}^{+1} - I_{+d}^{-1}) + (I_{-d}^{+1} - I_{-d}^{-1})}{(I_{+d}^{+1} - I_{+d}^{-1}) - (I_{-d}^{+1} - I_{-d}^{-1})}\right) \quad (1)$$

where $(I_{+d}^{+1} - I_{+d}^{-1})$ represents the difference of intensity between +1 and −1 order diffraction signals from a target structure with bias value +d and $(I_{-d}^{+1} - I_{-d}^{-1})$ represents the difference of intensity between +1 and −1 order diffraction signals from a target structure with bias −d.

Equation (1) can be re-written as:

$$Ov = d\left(\frac{As_{+d} + As_{-d}}{As_{+d} - As_{-d}}\right) \quad (2)$$

where $As_{+d}$ is an asymmetry value derived from the diffraction signals for the target structure with bias +d and $As_{-d}$ is an asymmetry value derived from the diffraction signals for the target structure with bias −d.

The above Equation (1) is derived from the assumption that there is linear relationship between asymmetry As and overlay error Ov:

$$As_{\pm d}=I_{\pm d}^{+1}-I_{\pm d}^{-1}=K*Ov \tag{3}$$

where K is a simple coefficient. In practice, an implementation may use a different model of the relationship. For example a sinusoidal model of the relationship is often used, in which case Equation (2) becomes:

$$Ov = \operatorname{atan}\left(\frac{As_{+d} + As_{-d}}{As_{+d} - As_{-d}} \cdot \tan(d)\right) \tag{2'}$$

In Equation (2'), the offset d is expressed as an angle, relative to $2\pi$ radians representing the period of the grating. For the purposes of the present description, the simple, linear model will be assumed. The skilled person can readily implement the same principles using a sinusoidal model or other preferred model, adapting the other Equation (3) as necessary.

In all the above equations, some scaling factors and normalization factors are omitted for simplicity. For example, as described in some of the prior published applications mentioned above, it may be convenient to normalize the differences between intensities using the average of those intensities as a denominator. So, for example, where above is written:

$$As_{\pm d}=I_{\pm d}^{+1}-I_{\pm d}^{-1} \tag{3}$$

the full expression might be:

$$As_{\pm d} = 2\left(\frac{(I_{\pm d}^{+1} - I_{\pm d}^{-1})}{(I_{\pm d}^{+1} + I_{\pm d}^{-1})}\right) = K*Ov \tag{3'}$$

The shorter expression will be used for convenience in the present disclosure, while the person skilled in the art can incorporate normalization and other practical details with routine skill and knowledge.

If each target structure were only one-dimensional, as in FIG. 4(a), then a single captured image 40 as shown in FIG. 5 has the complete information required to obtain independent measurements of overlay Ov with respect to the X and Y directions. In the case where a grating in the target has two-dimensional structure, however, the diffraction signals for different directions become mixed and inter-dependent as described above.

In terms of the mathematical model introduced above, the presence of additional orthogonal diffraction orders adds additional unknowns to the set of equations that must be solved to calculate Ov. Maintaining for now the simplicity of a linear model, the dependence of asymmetry value As on overly error incorporates an additional term, illustrated in Equation (4) below.

$$As=K_x*Ov_x+K_y*Ov_y+K_{xy}*Ov_x*Ov_y \tag{4}$$

Here we see that the asymmetry observed in the diffraction signals from a given target structure results from the effects of the overlay $Ov_x$ in the x direction and overlay $Ov_y$ in y direction, and additionally a "cross-term" dependent on overlay in both directions. Coefficients $K_x$ and $K_y$ express the sensitivity of asymmetry to overlay in each respective direction. A third coefficient $K_{yx}$ represents sensitivity to the cross-term (assuming for this explanation that the additional term depends also linearly on the product $Ov_x*Ov_y$). While these coefficients are represented in a mathematical model, their values are not known in advance, similar to the coefficient K in the one-dimensional example. The coefficient K is calculated (implicitly at least) when the Equation (2) or (2') is applied to calculate a measurement of overlay.

Considering the example metrology target 600 of FIG. 6, the number of target structures and combinations of programmed offsets in both directions, gives rise to the following four equations, representing asymmetry values for the four target structures 632, 633, 635 and 634 respectively:

$$As_{+dx+dy}=K_x*(Ov_x+dx)+K_y*(Ov_y+dy)+K_{xy}*(Ov_x+dx)*(Ov_y+dy)$$

$$As_{+dx-dy}=K_x*(Ov_x+dx)+K_y*(Ov_y-dy)+K_{xy}*(Ov_x+dx)*(Ov_y-dy)$$

$$As_{-dx+dy}=K_x*(Ov_x-dx)+K_y*(Ov_y+dy)+K_{xy}*(Ov_x-dx)*(Ov_y+dy)$$

$$As_{-dx-dy}=K_x*(Ov_x-dx)+K_y*(Ov_y-dy)+K_{xy}*(Ov_x-dx)*(Ov_y-dy) \tag{5}$$

The asymmetry values themselves are obtainable from the diffraction signals, extracted for example from an image of the type shown in FIG. 5. However, this set of four equations has five unknowns: Kx, Ky, Kxy, Ovx and Ovy, and so is not solvable with standard techniques.

The inventors have recognized that, by obtaining a second set of diffraction signals under different conditions, an additional set of equations can be added. This second set of diffraction signals results in the additional set of equations:

$$As'_{+dx+dy}=K'_x*(Ov_x+dx)+K'_y*(Ov_y+dy)+K'_{xy}*(Ov_x+dx)*(Ov_y+dy)$$

$$As'_{+dx-dy}=K'_x*(Ov_x+dx)+K'_y*(Ov_y-dy)+K'_{xy}*(Ov_x+dx)*(Ov_y-dy)$$

$$As'_{-dx+dy}=K'_x*(Ov_x-dx)+K'_y*(Ov_y+dy)+K'_{xy}*(Ov_x-dx)*(Ov_y+dy)$$

$$As'_{-dx-dy}=K'_x*(Ov_x-dx)+K'_y*(Ov_y-dy)+K'_{xy}*(Ov_x-dx)*(Ov_y-dy) \tag{6}$$

where the prime symbol ' indicates (observed) asymmetry values and (unknown) coefficients that are applicable to the second diffraction signals. The overlay values in each direction are the same for both sets of diffraction signals. Therefore the second diffraction signals bring four additional equations but only three additional unknowns. When combined with the previous set of equations (which had 5 unknowns), they can be solved for Ovx and Ovy.

FIG. 7 shows two images 740(1) and 740(2) obtained by two image capture steps in a method according to a first embodiment of the present disclosure. Each image captures diffraction signals from the target illustrated in FIG. 6, but using different capture conditions. Each image 740(1) and 740(2) is of the same form as that shown in FIG. 5, with four spatially separated images 702(1/2)-708(1/2) of the target. As described already for FIG. 5, each image 702(1/2) is formed of radiation diffracted by the target in the negative X direction and the positive Y direction (labelled −x/+y). Each image 706(1/2) is formed of radiation diffracted in the positive X direction and the negative Y direction (+x/−y). A spot indicates the region representing diffraction signals of the individual target structure 632 in each case. The difference between them is that images 702(1) and 706(1) are a record of first diffraction signals captured under first capture conditions while images 702(2) and 706(2) are a record of second diffraction signals captured under second illumination conditions different from the first illumination conditions.

The first and second capture conditions can differ in one or more parameters chosen from a wide variety of operating parameters of the inspection apparatus and its operation. For example the difference may be in illumination conditions used for the capture of diffraction signals, such that first illumination conditions and second illumination conditions differ in one or more of radiation wavelength, radiation polarization, and angular distribution of illumination. The difference may be not in the illumination conditions, or not only in the illumination conditions, but also there may be difference in conditions on the detection side. For example a wavelength filter, a difference in aperture and/or a difference in polarization can all be applied at the detection side, by suitable filters, for example. References to differences in capture conditions should therefore be understood to include any differences in the conditions, ranging from the source itself, through the illumination path and the collection path, and through to the detector and processing of signals.

Due to the different capture conditions used in capturing images 740(1) and 740(2), asymmetry values calculated from their diffraction signals will have different sensitivities to overlay in the different directions. First asymmetry values calculated from the first diffraction signals represented in image 740(1) can be used as asymmetry values As input to the equations (5) above, while second asymmetry values As', for the same target structures, can be calculated from the second diffraction signals in image 740(2) and used as input to the equations (6) above. With a total of 8 equations, the 8 unknowns can be calculated. These unknowns include the overlay errors $Ov_x$ and $Ov_y$ in the two directions, so that the desired overlay measurement can be obtained.

The obtained overlay measurement, for example OVy in case of the target shown in FIG. 6, will be subject to reduced sensitivity to variation of overlay in the second direction, even though the target structures have strongly two-dimensional features. Note also that the calculation, and the mathematical model underlying it, makes no assumption that a particular target structure or diffraction signal or asymmetry value is representing asymmetry and overlay in a particular direction. The calculation is therefore valid even when the effects of overlay in both directions are completely mixed in the captured diffraction signals. With the appropriate choice of bias scheme and solution of the sufficient number of simultaneous equations, the overlay error specific to each direction can be calculated to obtain a desired measurement. The design of target structures can of course be optimized so that a particular target gives a more reliable (accurate) measurement of overlay in one direction than the other. The primary periodicity will typically be the first direction in the language of the introduction and claims, and could be the X direction, the Y direction, or any arbitrary direction.

Application Example

FIG. 8 illustrates a method of measuring performance of a lithographic process using the apparatus and methods outlined above. In step S20, one or more substrates are processed to produce a metrology target including a plurality of target structures. The design of target can be for example the design shown in FIG. 6 and described above. Other designs are of course possible, including examples described below. Targets may be large target or small target designs, depending whether the first measurement branch or second measurement branch of the apparatus is to be used. Targets may comprise a plurality of target structures in distinct areas. For the purposes of the present description, it is assumed that overlay is of interest as a performance parameter of the lithographic manufacturing process.

At step S20 a substrate is loaded into an inspection apparatus, such as the inspection apparatus of FIG. 2. The substrate is one on which target structures (and optionally also functional device structures) have been produced using the lithographic manufacturing system of FIG. 1. For this purpose, a set of patterning devices will be provided, to define features of device structures and metrology targets through a series of patterning operations, interleaved with chemical and physical processing steps. One of these patterning devices will define, directly or indirectly, the first features of a plurality of target structures implementing the principles of the present disclosure. Another patterning device will define, directly or indirectly, the second features. The positions of the first and second features in the patterning devices include the programmed offsets for a two-dimensional bias scheme. If the lithographic tool used for some or all of the patterning steps uses a programmable patterning device, then the set of patterning devices may include one or more sets of patterning data, rather than physical reticles.

In step S21 metrology recipes are defined, including a recipe for a measurement of overlay using two or more sets of diffraction data, such as the ones captured in the images described above with reference to FIG. 7. All the usual parameters of such a recipe are defined, including the wavelength polarization, angular distribution and so forth of illuminating radiation.

In accordance with the principles of the present disclosure, the recipe defines two (or more) different sets of parameters, from which the first and second diffraction signals are obtained. In a first example, the difference between the first and second diffraction signals is the wavelength of the illuminating radiation. In other embodiments, different polarizations may be defined, or different angular distributions of illuminating radiation (illumination profiles) may be defined. As mentioned above, one also use different detection parameters, e.g. aperture or wavelength or polarization filtering in the detection path. In other embodiments, described below with reference to FIGS. 10 and 11, the recipes may specify different subsets of the target structures to be used for obtaining the first and second diffraction signals, under a single set of capture conditions.

In step S22, the inspection apparatus is operated to capture two or more sets of diffraction signals from the plurality of target structures. These may for be dark-field images (such as images 740(1) and 740(2) in FIG. 7) using the specified capture conditions/subsets.

As illustrated by the dotted box, third and further sets of diffraction signals can be obtained using yet further different capture conditions and/or target subsets. The mathematical discussion above have shown that by switching to a different capture condition, the variables $Ov_x$ and $Ov_y$ remain constant while other new unknowns are introduced. This means that, with every additional change of capture conditions, and thus the introduction of a new set of equations, the number of unknowns gets closer to the number of equations. In a case where, when using the first and second diffraction signals together, there remain more unknowns than equations the process can be repeated with third diffraction signals, fourth diffraction signals up to any number. With enough changes, the number of equations becomes equal to the number of unknowns and thus the equations can be solved. Thus this method can be applied to any mathematical model that has any number of unknowns: enough equations can be generated as long as the number of available wavelengths permits additional items.

A different model may imply a greater number of coefficients, requiring additional diffraction signals to solve a system having more than eight unknowns. Even in the case of a linear model featuring coefficients $K_x$, $K_y$ and $K_{xy}$, which is solved by the two sets of four asymmetry values, additional accuracy in the measured overlay values can result from capturing additional diffraction signals and solving a larger set of equations for the parameters of interest. For example, using three or four target structures to obtain a third set of diffraction signals one can construct a system of equations in 11 unknowns: the 8 mentioned above plus three new K values. Provided three, four or more new asymmetry values are obtained, with only three new additional coefficients. Adding another capture with third diffraction signals will therefore bring additional accuracy to the measurements of the parameters of interest, such as overlay.

It goes without saying, any of these captures may in practice be performed multiple times, with the result being averaged to reduce random noise. It will also be understood that the captures may be repeated for multiple targets across the substrate.

At step S23 asymmetry values As and As' are calculated from the captured diffraction signals of the various target structures. In the example using dark-field imaging and segmented illumination and detection optics, these asymmetry values can be derived by selecting and combining pixel intensities from different regions of interest within one or more dark-field images. First asymmetry values As can be calculated from the first diffraction signals captured in image 740(1), while second asymmetry values As' can be can derived from the second diffraction signals captured in image 740(2).

At step S24, once sufficient asymmetry values have been obtained for the number of unknowns, the full set of equations can be solved to calculate one or more parameters of interest relating to the target structures and/or relating to the performance of the lithographic process by which the target structures have been formed. Parameters of interest include in particular the directional overlay values $Ov_x$ and $Ov_y$. Parameters of interest may be simply whether the image of a target structure contains a mixture of radiation diffracted in two directions or not. The value of cross-coefficient $K_x$ relative to $K_x$ and/or $K_y$ can be used, for example, as an indicator of significant two-dimensional character.

Note that any resulting set of equations in any of the aforementioned methods can be solved by using numerical techniques, and does not require an analytical solution. Solution for all the variables may be left as merely an implicit step, while only the parameters of interest (e.g. overlay Ov in one or both directions) are calculated and output explicitly.

At step S25, the metrology recipe may be updated in response to the obtained measurements and ancillary data. For example, the metrology techniques for a new product or target layout may be under development. Information about the two-dimensional characteristics can be used to select a more appropriate recipe.

In step S26, in a development and/or production phase of operating the lithographic production facility of FIG. 1, recipes for the lithographic process may be updated, for example to improve overlay in future substrates. The ability to measure overlay more accurately in one or both different directions allows more effective corrections to be developed and applied. The techniques disclosed herein are fully compatible with the efficient measurement techniques using segmented illumination and segmented detection systems, including when target structures have significant two-dimensional structure. An inspection apparatus can be used with a fixed, segmented detection system, while covering a full range of targets, reducing cost and size of the apparatus.

The calculations to obtain measurements, and to control the selection of wavelengths and other recipe parameters, can be performed within the image processor and controller PU of the inspection apparatus. In alternative embodiments, the calculations of asymmetry and other parameters of interest can be performed remotely from the inspection apparatus hardware and controller PU. They may be performed for example in a processor within supervisory control system SCS, or in any computer apparatus that is arranged to receive the measurement data from the processor and controller PU of the inspection apparatus. Control and processing of the calibration measurements can be performed in a processor separate from that which performs high-volume calculations using the correction values obtained. All of these options are a matter of choice for the implementer, and do not alter the principles applied or the benefits obtained. Use of the term "processor" in the description and claims should be understood also to encompass a system of processors.

Additional Example of First Embodiment

FIG. 9 illustrates (a) a target 900 similar to the target 600 of FIG. 6 and (b) implementation of part of the method of FIG. 8 using such a target. The target 900 comprises four target structures 932, 933, 934, 935. Each target structure in this example has the X direction as its primary direction of periodicity, and is intended for accurate measurement of overlay $Ov_x$ in the X direction. Segmentation in the Y direction may be present but is not visible on the scale of the drawing. Programmed offsets in X and Y directions are included in the relative placement of the first and second features in each target structure. As shown by labels "+dx+dy" etc., these offsets implement a bias scheme with four combinations of offset the same as the one shown in FIG. 6.

As shown in FIG. 9 (b), in step S22 two sets of diffraction signals are captured from the four target structures. When using the inspection apparatus of FIG. 2, all four target structures 933-935 are illuminated simultaneously within the illumination spot 931. The inspection apparatus captures first and second diffraction signals in two dark-field images 740(λ1) and 740(λ2). The dark-field images in this example are examples of the images 740(1) an 740(2) shown in FIG. 7. The index labels λ1 and λ2 indicate that the wavelength of radiation used to capture the first and second diffraction signals is different. Predictably, the result will be a difference in the angle of spread of the diffraction orders from the gratings formed by the first and second features. Importantly, however, the interaction of the radiation with the stack of layers defining the target structures may be different in a number of ways, not necessarily predictable or known. Particular differences in interaction can result from the three-dimensional nature of the target structure, in which the thickness and material properties of the layers L1 and L2 and intervening layers all influence propagation of the inspection radiation. Each set of diffraction signals will be sensitive in different ways to overlay and to process variations in the different parameters. In terms of the mathematical model presented above, the coefficients K' will be different when using the second wavelength than coefficients K when using the first wavelength.

In step S23 first and second asymmetry values As and As' are derived for each target structure. These are combined in step S24 to obtain a measurement of overlay in at least the first direction, being the X direction in this example.

Depending on the construction of the inspection apparatus, the first and second diffraction signals can be captured sequentially or simultaneously. Selection of wavelengths can be through color filter 12b, or by a tunable or switchable source 11. Illumination with multiple wavelengths could be used, with filtering at the detection side. The choice of wavelengths can be made based on calculation and/or experiment with the designs of target structure, with the aim of ensuring a significant difference between the first coefficients K and the second coefficients K', thereby to maximize the information content of the asymmetry values when combined together. Other examples of the first embodiment can be made by switching other parameters such as the polarization (filter 12c) or angular distribution (aperture device 13) of the illumination system. As mentioned, parameters can also be switched in the detection system, in addition to or as an alternative to the illumination system.

Second Embodiment

FIG. 10 illustrates (a) a different form of target and (b) implementation of part of the method of FIG. 8 using such a target in a second embodiment. The target 1000 comprises eight, rather than four, target structures. The eight target structures are divided into two distinct subsets, indicated by suffixes 'a' and 'b'. As in FIG. 9, each target structure in this example has the X direction as its primary direction of periodicity, and is intended for accurate measurement of overlay $Ov_x$ in the X direction. Segmentation in the Y direction may be present but is not visible on the scale of the drawing. A first subset of target structures comprises four target structures 1032a, 1033a, 1034a and 1035a. A second subset of target structures comprises four target structures 1032b, 1033b, 1034b and 1035b. Within each subset, programmed offsets in X and Y directions are included in the relative placement of the first and second features in each target structure. As shown by labels "+dx+dy" etc., these offsets implement in each subset a bias scheme with four combinations of offset the same as the one shown in FIG. 6.

As shown in FIG. 10 (b) in conjunction with FIG. 11, in step S22 two sets of diffraction signals 740(a) and 740(b) are captured. The capture conditions in this embodiment are assumed to be the same for both the first diffraction signals and the second diffraction signals. This may reduce measurement time. The difference between the first and second diffraction signals is achieved by a difference in design between the first and second subsets of target structures. It will be seen that the eight target structures are made smaller in the second direction, so that they can all fit within the same illumination spot 1031 and field of view of the apparatus. In this way, both sets of diffraction signals can be captured from regions within a single dark-field image 740(a/b). If preferred, the target structures could be kept at the same size as the targets 600 and 900, but additional capture steps would then be required to obtain a full set of diffraction signals, and additional errors could be introduced through inconsistency of the capture conditions.

The inspection apparatus in this example captures first and second diffraction signals 740(a) and 740(b) and the index labels a and b indicate that the target structure design used to capture the first and second diffraction signals is different. Any kind of difference that can be reliably produced in the lithographic process may be considered. The target structures may have different pitches and/or duty cycles in one or both of the directions. As another simple difference, one subset of target structures may have a "line on line" layout while the other subset has a "line on trench" layout. In a line on line layout, the second features lie directly on top of corresponding first features, as shown in the FIG. 6 (b) cross-section. In the line on trench layout, the second features lie over the spaces between the first features. In any case, the interaction of the radiation with the stack of layers defining the target structures may be different in a number of ways between the two subsets of target structures, in ways which are not necessarily predictable or known. Each set of diffraction signals will be sensitive in different ways to overlay and to process variations in the different parameters. In terms of the mathematical model presented above, the coefficients K' will be different for the second subset than coefficients K for the first subset.

In step S23 a first asymmetry value As is derived for each target structure 1032a-1035a within the first subset, and a second asymmetry value As' are derived for each target structure within the second subset. These four values As and four values As' are combined in step S24 to obtain a measurement of overlay in at least the first direction, being the X direction in this example.

It will be understood that third, fourth and further subsets with further different designs can be included, if third, fourth etc. sets of diffraction signals are required. Additionally, the techniques of the first and second embodiments can be combined so that, for example, two different capture conditions are used to obtain diffraction signals from two different subsets of target structures. Immediately this yields four set of diffraction signals. By proper design of the different subsets and by proper and choice of capture conditions, additional unknowns can be solved. Alternatively, rather than solving a single large set of equations, independent calculations of the overlay error can be made using (say) first and second diffraction signals together and third and fourth diffraction signals together. In this way, without complicating the mathematical model and its solution, the same Ov values can be measured multiple ways, and combined to increase the overlay accuracy performance of the inspection apparatus.

Finally, as mentioned above, while the above techniques can be used to measure a property of the target independently in two directions, it may also be used as a simple check to see whether significant two-dimensional structure in both sets of features is present or not. If not, then a single set of diffraction signals may be sufficient for measurement of further targets, saving time. If significant two-dimensionality is present, indicated for example by a significant value $K_{xy}$ in one of both sets of diffraction signals, then the techniques of the present disclosure can be applied to obtain accurate measurements of overlay in one or both directions.

Modified Embodiment

FIG. 12 illustrates (a) a target 1200 similar in function to the target 1200 of FIG. 6, but with modifications that will now be described. The target 1200 comprises four target structures 1232, 1233, 1234, 1235. Each target structure in this example has the both the X direction and the Y direction as primary directions of periodicity. As a simple example, each first feature 1262 may comprise a square structure on the substrate with X-Y dimensions 200 by 200 nm, and the pitch Px and Py may be 800 nm in both directions. Each of the first features and each of the second features therefore has the same dimension in both the X direction and the Y direction. In alternative implementations, the dimensions and/or the pitch can be made different in the two directions. It will be understood that the features and their spacing are represented schematically, and are not shown to scale, nor in their true numbers. As in the previous examples, each first feature and/or each second feature may be sub-segmented into smaller features, in one or two directions, this sub-segmentation not being visible on the scale of the drawing. In the following examples, the first and second features will be illustrated and described as if they are unitary features, purely for simplicity. Programmed offsets in X and Y directions are included in the relative placement of the first features 1262 and the second features 1264 in each target structure. As shown by labels "+dx+dy" etc., these offsets implement a bias scheme with four combinations of offset. The combinations are the same as the ones shown in FIG. 6, but arranged in a different relationship to one another. The bias scheme of FIG. 6 is equally suitable, as will be understand from a consideration of the principles explained below. Also, this target is designed to have a high degree of symmetry, to reduce sensitivity to aberrations of the optical system, and to make it compatible with a existing metrology methods and apparatuses.

A main difference between the FIG. 12 target and the ones described above is that the target structures are formed in one continuous array. FIG. 12 (*b*) shows one layer of the target 1200, comprising the first features 1262 only. This may be for example the bottom layer of the overly metrology target 1200. As can be seen, the first features 1262 are formed in a continuous periodic array, with no gaps between distinct target structures. FIG. 12 (*c*) is an enlarged view of a central portion of the target 1200, corresponding to the dashed circle in FIGS. 12(*a*) and (*b*). Here it can be seen that the four target structures 1232, 1233, 1234, 1235 are simply four regions of this larger, continuous array, in which the programmed positional offset (overlay bias) is different from one region to the next. The programmed positional offset in each region can be represented conveniently by bias vectors, which are shown in each region of FIG. 12 (*c*).

In the illustrated example, it is assumed that the first features define the bottom layer of the overlay metrology target, and the second features are in a top layer, applied subsequently. The programmed offsets are in the placement of the second features 1264 in each region, while the array of first features is entirely regular. This is only one possible example, however, and the programmed offsets may be in the bottom layer, in the top layer or in both. One benefit of providing the features of the bottom layer in a continuous array is to reduce the process effects impacting this structure. Furthermore, any process variations that are to be corrected can be modelled over the complete target. In certain processes and designs, however, there may be benefits to putting the programmed offsets in the first layer, and a regular array in the top layer.

There is in principle a risk that the diffraction signals will include cross-talk due to edge effects between the different target structures. The absence of gaps between the target structures, and the uniformity of the array in both directions are factors that may help to reduce edge effects. Moreover, the selection of which target structures to place next to one another in the metrology target can also be done so as to reduce noise due to edge effects. As seen by the vectors in FIG. 12 (*c*), for example, the arrangement is such that each target structure has two immediate neighbors. The bias scheme is designed so that the programmed offset of each target structure is intermediate between the programmed offsets of its immediate neighbors. In terms of the bias vectors, the bias vector rotates only 90 degrees from each target structure to the next. The target structures may be considered to be arranged in a ring, which can be traversed clockwise or counter-clockwise, with the bias vector stepping always by at most 90 degrees. The arrangement avoids having a common border between, for example, two target structures with bias vectors pointing in opposite directions. While edge effects are inevitable when radiation is diffracted by a finite structure, careful design can minimize them. By minimizing edge effects, the signal noise can be reduced, or other constraints can be relaxed. For example, the overall size of the metrology target may be able to be reduced, and/or the positional accuracy of the target and the regions of interest (ROI) can be relaxed.

FIG. 13 illustrates just the central detail from a metrology target 1300 that is a further modification of the metrology target of FIG. 12. In this example, narrow transition zones 1302 are provided between the neighboring target structures, in which the bias vector is intermediate between the bias vectors of the target structures to either side. Such a transition zone, although it is "wasted space" from one point of view, can help to improve accuracy by reducing edge effects. In principle, the variation of bias could be continuous from each feature to the next, without deviating from the principles of the present disclosure. In such a case, however, the signals may become too sensitive to errors in placement of the regions of interest ROI.

Third Embodiment

FIG. 14 (*a*) shows a metrology target 1400 according to a third embodiment of the present disclosure. In detail, the target has the same basic structure as the targets 1200 and 1300 described above. That is to say, a plurality of target structures are formed as neighboring regions of a larger, continuous array. In this target, however, the number of regions is greater than four, and comprises eight outer regions arranged in a ring around a central region. Numbering from the top left and proceeding counter-clockwise, the eight outer regions form respective target structures 1432-1 to 1432-8. As in the previous example, a programmed positional offset (overlay bias) is different from one region to the next. The programmed positional offset in this example is represented conveniently by a bias vector, which is shown in each region of FIG. 14 (*a*). The central region optionally provides forms a central target structure 1432-0. As described below, the central target structure may be used for different purposes. For the present, it may be assumed to have a zero bias, represented by a simple dot.

The form of the first features and second features may be assumed to be the same as in the examples of FIGS. 12 and 13 (feature size 200×200 nm and pitch Px=Py=800 nm). If the overall size of each continuous array is the same as in FIG. 12, then of course each target structure will be smaller. Alternatively, the overall size of the target can be increased to achieve a desired size of individual target structure. The overall size in one example is 16×16 μm.

In the terminology of the introduction and claims, the eight target structures 1432-1 to 1432-8 together provide both the first subset of target structures and the second subset of target structures in one metrology target. All eight target structures can be imaged in a single capture step, if desired, and the diffraction signals from all the target structures can be processed as one large set. The division into subsets in such an embodiment is to some extent arbitrary, since the only difference between them is the overlay bias applied. For the purposes of the present description, however, it is convenient to consider that the odd-numbered target structures (1432-1, -3, -5, -7) form a first subset and the even-numbered target structures (1432-2, -4, -6, -8) form a second subset. It will be seen that the bias scheme of the first subset of target structures is the same as the bias scheme of the target 1200 in FIG. 12.

The second subset of target structures (1432-2, -4, -6, -8), are positioned with each one in between two target structures of the first subset. The bias scheme of the second subset is such that each target structure has a programmed offset in the X and Y directions that is intermediate between its neighbors on either side. As a result, any target structure bordering two neighboring target structures has a programmed offset intermediate between the programmed offsets of those two neighboring target structures (disregarding the central region which is not one of the target structures for this purpose). In terms of bias vectors, it will be seen that the bias vector now rotates less than 90 degrees between neighboring target structures. More particularly, in this example, the bias vector representing said programmed offset rotates 45 degrees between neighboring target structures.

The progressive change of the programmed offset from neighbor to neighbor, together with the use of a single continuous array of features has the benefit of reducing edge effects, in the same manner as described already about for the examples of FIGS. 12 and 13. As already explained, this mitigates the loss of allows signal quality that would normally be incurred by fitting a greater number of targets to be fitted into a smaller total area. Effectively, the detailed structure of target 1400 is the same as shown in FIG. 13, but with the transition zones 1310 wide enough to form target structures in their own right. Narrow transition zones (not shown) could be provided between the regions in metrology target 1400, the same manner as in FIG. 13. The transition zones would have bias angles rotated less than 45 degrees from the target structures on either side.

Referring now to FIG. 14 (*b*), this shows part of a multiple image 1440 of the target, captured by the apparatus of FIG. 4 with spatial separation of diffraction orders. To save space, only the +1 and −1 diffraction order images are shown, and labeled 1440(+1) and 1440(−1) respectively. The signals are processed in essentially the same manner as in the first and second embodiments, except that sufficient diffraction signals for an overlay measurement are obtained from a single capture of the composite metrology target 1400. This does not exclude the possibility of increasing accuracy by obtaining additional diffraction signals using different radiation characteristics. Nor does it exclude the possibility of providing additional targets with different design parameters. It just means that sufficient signals to solve the required system of equations can be obtained from the signal diffraction image 1440.

FIG. 14(*b*) is overlaid with a schematic representation of signal processing to obtain asymmetry values As from the eight target structures. A first asymmetry value $As_1$ is obtained by comparing the opposite order diffraction signals from regions of interest (ROI) corresponding to the top right target structure 1432-7. As another example, a fourth asymmetry value $As_4$ is obtained by comparing the opposite order diffraction signals from regions of interest (ROI) corresponding to the bottom left target structure 1432-3. Numbers in circles identify the correspondence between each target structure and a respective asymmetry value $As_i$, given a total of eight asymmetry values from the single diffraction image.

Given these eight asymmetry values $As_1$ to $As_8$ obtained as shown in FIG. 14 (*b*), overlay can be determined by solving a system of equations similar to those described above. For the present example, the equations implement a sinusoidal model of the relationship between asymmetry value and overlay, rather than the simple linear approximation. The set of equations for the target 1400 is thus:

$$AS_1 = K_x \sin\left(\frac{2\pi}{P}(OV_x + d_x)\right) + K_y \sin\left(\frac{2\pi}{P}(OV_y + d_y)\right) +$$
$$K_{xy} \sin\left(\frac{2\pi}{P}(OV_x + d_x)\right)\sin\left(\frac{2\pi}{P}(OV_y + d_y)\right)$$

$$AS_2 = K_x \sin\left(\frac{2\pi}{P}(OV_x + d_x)\right) + K_y \sin\left(\frac{2\pi}{P}(OV_y - d_y)\right) +$$
$$K_{xy} \sin\left(\frac{2\pi}{P}(OV_x + d_x)\right)\sin\left(\frac{2\pi}{P}(OV_y + d_y)\right)$$

$$AS_3 = K_x \sin\left(\frac{2\pi}{P}(OV_x - d_x)\right) + K_y \sin\left(\frac{2\pi}{P}(OV_y + d_y)\right) +$$
$$K_{xy} \sin\left(\frac{2\pi}{P}(OV_x + d_x)\right)\sin\left(\frac{2\pi}{P}(OV_y + d_y)\right)$$

$$AS_4 = K_x \sin\left(\frac{2\pi}{P}(OV_x - d_x)\right) + K_y \sin\left(\frac{2\pi}{P}(OV_y - d_y)\right) +$$
$$K_{xy} \sin\left(\frac{2\pi}{P}(OV_x - d_x)\right)\sin\left(\frac{2\pi}{P}(OV_y - d_y)\right)$$

$$AS_5 = K_x \sin\left(\frac{2\pi}{P}(OV_x + d_x)\right) + K_y \sin\left(\frac{2\pi}{P}(OV_y)\right) +$$
$$K_{xy} \sin\left(\frac{2\pi}{P}(OV_x + d_x)\right)\sin\left(\frac{2\pi}{P}(OV_y)\right)$$

$$AS_6 = K_x \sin\left(\frac{2\pi}{P}(OV_x - d_x)\right) + K_y \sin\left(\frac{2\pi}{P}(OV_y)\right) +$$
$$K_{xy} \sin\left(\frac{2\pi}{P}(OV_x - d_x)\right)\sin\left(\frac{2\pi}{P}(OV_y)\right)$$

$$AS_7 = K_x \sin\left(\frac{2\pi}{P}(OV_x)\right) + K_y \sin\left(\frac{2\pi}{P}(OV_y + d_y)\right) +$$
$$K_{xy} \sin\left(\frac{2\pi}{P}(OV_x)\right)\sin\left(\frac{2\pi}{P}(OV_y + d_y)\right)$$

$$AS_8 = K_x \sin\left(\frac{2\pi}{P}(OV_x)\right) + K_y \sin\left(\frac{2\pi}{P}(OV_y + d_y)\right) +$$
$$K_{xy} \sin\left(\frac{2\pi}{P}(OV_x)\right)\sin\left(\frac{2\pi}{P}(OV_y + d_y)\right)$$

If we assume that the ninth region provides a target structure 1432-0 with zero bias, the equation for its asymmetry value $As_0$ would be a linear combination of the above eight equations and does not add information. In matrix notation, the matrix rank remains 8, with or without the 'no-bias' case. This raises the possibility to use the central region for other purposes, as will be described below.

FIG. 15 illustrates implementation of part of the method of FIG. 8 using such a target in accordance with the third embodiment of the present disclosure. In step S23 asymmetry values As for both first subset of the target structures and the second subset of the target structures are obtained from the captured diffraction signals. The illustration shows these being treated as a single set of asymmetry values for further calculation. Rather than requiring separate captures.

Because all the target structures have the same target design parameters and the diffraction signals are all captured with the same radiation characteristics, there is no difference in coefficients K or period P, between the different target structures. In other words, there are only five unknowns and, in principle, only five of these equations should be sufficient to solve all unknowns. However, it may be expected that increased accuracy can be obtained by using six, seven or eight. If using fewer than eight, it would be recommended to choose target structures having a good balance of programmed offsets in both directions. This is easier to achieve if one uses more than 5 values. In other embodiments, however, the number of target structures over the first and second subsets may be fewer than eight in any case.

Numerous variations of the metrology target 1400 can be envisaged, without departing from the principles set forth above. The regions defined by different programmed offsets do not all have to be equal in size. Some could be larger, to give higher signal quality, while others are smaller. For example, it could be decided to provide a smaller area for target structures with mixed (X and Y) biases, and larger areas to provide more emphasis on single direction bias. (The central region can be smaller, too. The regions do not need to be square. The examples shown have bias vectors of different lengths, depending whether the target structure has a mixed (X and Y) positional offset, or a single direction offset (X only or Y only). As another modification, the magnitude of the offset in each direction could be different between different target structures for example to make the bias vectors more equal in length. For example, to have a uniform length of bias vector of 20 nm, the bias in target structure 1432-8 may be for example (0, 20), while the bias vector in target structure 1432-7 would be $(20/\sqrt{2}, 20/\sqrt{2})$, or approximately (14, 14). As another variation, the single bias target structures could be arranged at the corners of the target, with the mixed bias regions in between.

Additionally, as mentioned, the central regions which are not used for overlay measurement target structures can be used for additional purposes. As one example of this, instead of a zero-bias overlay target, the second features (top-grating) can be omitted entirely. This enables a measurement of the first layer by itself, so that asymmetry value $AS_0$ provides a measurement of bottom-grating asymmetry as a useful performance parameter. In alternative embodiments, the bottom-grating could be left-out, or both gratings.

Modified Third Embodiment

FIG. 16 (a) illustrates an enlarged metrology target according to a modified third embodiment of the present disclosure. FIG. 16 (b) shows part of a multiple image of the target, captured by the apparatus of FIG. 4. In detail, the target has the same basic structure as the targets 1200, 1300 and 1400, described above. That is to say, a plurality of target structures 1632-1 etc, are formed as neighboring regions of a larger, continuous array. In this target, however, the number of regions is 49, arranged in a square array of 7×7 regions. The programmed positional offset is again represented conveniently by a bias vector, which is shown in each region. The bias scheme is again such that any target structure bordering two neighboring target structures has a programmed offset intermediate between the programmed offsets of those two neighboring target structures (disregarding the regions with zero bias, which are not one of the target structures for this purpose). In terms of bias vectors, it will be seen that the bias vector again rotates less than 90 degrees between neighboring target structures. Again, in this example, the bias vector representing said programmed offset rotates 45 degrees between neighboring target structures. Also, this target is designed to have 180-degree rotational symmetry, to reduce sensitivity to aberrations of the optical system, and for compatibility with other metrology methods.

The form of the first features and second features may be assumed to be the same as in the examples of FIGS. 12 and 13 (feature size 200×200 nm and pitch Px=Py=800 nm). If the overall size of each continuous array is the same as in FIG. 12, then of course each target structure will be smaller. Alternatively, the overall size of the target can be increased to achieve a desired size of individual target structure. The overall size in one example is 16×16 μm.

In FIG. 16 (b), the corresponding portions of the diffraction image are again numbered, to show which diffraction signals yield which of the asymmetry values $As_1$ to $As_8$ in the equations above. Each different programmed offset occurs at least four times in different target structures across the array. Four of the programmed offsets occur more times. This provides redundancy of signals for solving the eight equations. This redundancy can be exploited in a number of different ways, which will now be described.

The 44 target structures (regions having non-zero programmed offsets) can be viewed in different groups. These different groups can be used as overlay targets for different layer pairs in a device manufacturing process. The first features can be made in a continuous array in a first layer, for example, and then the second features in a can be added in a second layer over a first part of the array to define a first group of target structures. Second features can be added over a second part of the array to define a second group of target structures, and so on. Provided each group has a set of five or more different programmed offsets, for example seven or eight different programmed offsets, the first group of target structures can be used to measure overlay for the second layer over the first layer, while the second group of target structures can be used to measure overly for the third layer over the first layer.

Referring now to FIG. 17, two different options are illustrated for choosing such groups, given the basic design of target 1600. Referring to FIG. 17 (a), it will be noticed that some of the target structures define closed rings with their neighbors, each one similar in layout to the target 1400. Four groups can be defined as shown by the boundaries labeled 1700-1 to 1700-4. Each of these groups contains the full set of eight programmed offsets. FIG. 17 (b) shows another sub-division of the same basic target design into groups. As shown by the boxes labeled 1702-1 to 1702-4, the first, third, fifth and seventh rows of regions can be used to provide four groups of target structures in which the target structures of each group are arranged in a line. Each of the lines contains seven of the set of eight different programmed offsets. As mentioned above, anything from five to eight different programmed offsets will be enough to solve the system of equations necessary for an overlay measurement.

Within each group, any target structure bordering two neighboring target structures has a programmed offset intermediate between the programmed offsets of those two neighboring target structures. Therefore, each group of target structures effectively can be used as an independent metrology target and can be assigned to a different top- or bottom-grating (multi-layer target). As mentioned already, if it suits a particular process, it may be the top grating that is formed as a continuous array without positional offsets, while the programmed offsets are included in lower layers formed before the top layer.

Instead of using different groups for different layers, the redundancy in the target of FIG. 16 can be exploited to obtain additional information relating to a single layer pair.

For example, the results from a single bias value, measured at different locations on the target, can be used for correcting process variations that may occur over the area of the target, or variations in the inspection tool itself, such as in homogeneity of the radiation spot. While groups are shown in FIG. 17 as squares or lines of neighboring target structures, other schemes are possible in which a group comprises target structures distributed widely, even randomly across the larger target.

The numerous variations described above in relation to the third embodiment can be applied equally in the modified third embodiment.

The central no-bias regions can again be used to measure bottom grating asymmetry or other parameters. Where the larger target provides multiple such regions, the variation of these parameters can be measured across the target. The central no-bias regions can of course be used as additional input to overlay calculations, to improve robustness against effects such as grating asymmetry.

CONCLUSION

The principles disclosed above allow measurement accuracy to be maintained when target structures have two-dimensional characteristics in both first features and second features. The technique is suitable for application in asymmetry measurements to be made by dark field imaging methods, using segmented detection systems, as well as other methods. Use of two or more sets of capture conditions, and/or two or more different designs of target structure allows the simple and efficient inspection apparatus based on a segmented detection system to operate with a wider range of target designs, including those having significant diffraction in a second direction in both layers.

Additionally, the disclosed method and apparatus can deliver information about the two-dimensional character of the target structures. Such information may in practice be unknown, prior to inspection.

With regard to the third embodiment, a single acquisition from a composite metrology target can determine 2D overlay. This third embodiment can be extendibility to multi-layer target design.

The embodiments based on continuous array structures can reduce noise and process dependency, as well as enabling intra-target/inter-grating correction of process effects.

The arrangement of target structures with progressive bias differences helps reduce edge-effects between gratings, enabling larger ROI selection and/or reduced overall target size.

Additional measurements of parameters such as bottom grating asymmetry can be integrated into the target design.

While specific embodiments of the invention have been described above, it will be appreciated that the invention may be practiced otherwise than as described.

While the inspection apparatus or tool illustrated in the embodiments comprises a particular form of scatterometer having first and second branches for simultaneous imaging of pupil plane and substrate plane by parallel image sensors, alternative arrangements are possible. Rather than provide two branches permanently coupled to objective lens 16 with beam splitter 17, the branches could be coupled selectively by a movable optical element such as a mirror. The optical system could be made having a single image sensor, the optical path to the sensor being reconfigured by movable elements to serve as a pupil plane image sensor and then a substrate plane image sensor.

While the optical system illustrated in FIG. 2 comprises refractive elements, reflective optics can be used instead. For example the use of reflective optics may enable the use of shorter wavelengths of radiation.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the inspection apparatus hardware and suitable target structures realized on patterning devices and on patterned substrates, an embodiment may include a computer program containing one or more sequences of machine-readable instructions implementing methods of measurement of the type illustrated above to obtain information about a target structure and/or about a lithographic process. This computer program may be executed, for example, within image processor and controller PU in the apparatus of FIG. 2 and/or the control unit LACU of FIG. 1. There may also be provided a data storage medium (e.g., semiconductor memory, magnetic or optical disk) having such a computer program stored therein.

Further embodiments according to the invention are described in below numbered clauses:

1. A method of determining overlay performance of a lithographic process, the method including the following steps:

(a) obtaining a plurality of target structures that have been formed by the lithographic process, each target structure comprising a set of first features arranged periodically in at least a first direction and a set of second features arranged periodically in at least the first direction and being subject to overlay error in the placement of the second features relative to the first features, (b) using a detection system to capture first diffraction signals comprising selected portions of radiation diffracted by at least a subset of the target structures;

(c) using the detection system to capture second diffraction signals comprising selected portions of radiation diffracted by at least a subset of the overlay targets;

(d) processing asymmetry information derived from the first diffraction signals and the second diffraction signals to calculate at least a measurement of said overlay error in at least the first direction, wherein said target structures have been formed with programmed offsets in the placement of the second features relative to the first features in addition to said overlay error, the programmed offsets within each subset differing in both the first direction and in a second direction, the first and second directions being non-parallel, and wherein the calculation of overlay error in step (d) combines said asymmetry information with knowledge of said programmed offsets while making no assumption whether asymmetry in a given target structure results from relative displacement of the second features in the first direction, in the second direction or both directions.

2. A method according to clause 1 wherein the first diffraction signals are captured in step (b) under first capture conditions and the second diffraction signals are captured in step (c) under second capture conditions different from the first capture conditions.

3. A method according to clause 2 wherein said first capture conditions and said second capture conditions differ in one or more of the wavelength, polarization, and angular distribution of radiation used for illumination and/or detection of the target structures.

4. A method according to clause 1, 2 or 3 wherein the first diffraction signals captured in step (b) comprise radiation diffracted by a first subset of target structures and the second diffraction signals captured in step (c) comprise radiation diffracted by a second subset of target structures different from the first subset of target structures.

5. A method according to clause 4 wherein the target structures of said first subset and the target structures of said second subset differ in one or more of pitch, feature size, relative placement, and segmentation in the second direction.

6. A method according to clause 4 wherein the target structures of said first subset and the target structures of said second subset differ only in the combinations of programmed offsets in both the first direction and the second direction, the number of combinations of programmed offsets available over both subsets being greater than four.

7. A method according to clause 6 wherein target structures of the first and second subsets are arranged together a composite metrology target, the layout of target structures being such that a bias vector defined by the programmed offsets in the first and second directions varies progressively from each target structure to its neighbors.

8. A method according to any of clauses 1 to 7 wherein each of said first features and said second features comprises a feature whose dimension is the same in the first direction as in the second direction.

9. A method according to any preceding clause wherein each of said first features and said second features comprises an elongate feature extending transverse to the first direction and being segmented periodically in the second direction.

10. A method according to clause 9 wherein the segmentation of the elongate first and second features has a period different to a period of spacing of the first and second features.

11. A method according to any preceding clause wherein the first features of at least the first subset of target structures are formed in a first continuous array and the second features of the first subset of target structures are formed in a second continuous array of features, the different target structures being defined by variation of said positional offsets over one or other of said continuous arrays.

12. A method according to any preceding clause wherein the calculation of overlay error in step (d) derives from the first diffraction signals a first asymmetry value for each of at least four target structures and derives from the second diffraction signals a second asymmetry value for each of at least four target structures, and uses at least the derived first and second asymmetry values to solve equations in more than four unknowns, one of said unknowns being the measurement of overlay error in the first direction.

13. A method according to any preceding clause wherein the calculation of overlay error in step (d) derives from the first and second diffraction signals an asymmetry value for five or more target structures, and uses at least the derived asymmetry values to solve equations in more than four unknowns, one of said unknowns being the measurement of overlay error in the first direction.

14. A method according to clause 13 wherein the calculation of overlay error in step (d) derives from the first and second diffraction signals an asymmetry value for seven or more target structures, and uses at least the derived first and second asymmetry values to solve equations in more than four unknowns, one of said unknowns being the measurement of overlay error in the first direction.

15. A method according to any preceding clause further comprising a step:
(c2) using the detection system to capture third diffraction signals comprising selected portions of radiation diffracted by at least a subset of the overlay targets,
and wherein the step (d) includes processing asymmetry information derived from the first diffraction signals, the second diffraction signals and the third diffraction signals to calculate a measurement of said overlay error in at least the first direction.

16. A method according to clause 15 wherein the calculation of overlay error in step (d) uses the first diffraction signals to derive an asymmetry value for each of at least four target structures, uses the second diffraction signals to derive an asymmetry value for each of at least four target structures and uses the third diffraction signals to derive an asymmetry value for each of at least three target structures, and uses more than eight of the derived asymmetry values to solve equations in more than eight unknowns, one of said unknowns being the measurement of overlay error in the first direction.

17. A method according to any of clauses 12 to 16 to wherein the calculation of overlay error in step (d) calculates a measurement of overlay error in the second direction.

18. A method according to any preceding clause wherein in step (b) said first diffraction signals for said plurality of target structures are captured using a detection system to form one or more first images of the plurality of target structures, in step (c) said second diffraction signals for the plurality of target structures are captured using the detection system to form one or more second images of the plurality of target structures, and in step (d) a first asymmetry value for each target structure is derived from intensity values in respective portions of said first image or images and a second asymmetry value is derived from intensity values in respective portions of said second image or images.

19. A method according to clause 18 wherein each of said first and second images contains complementary portions which are images of the same plurality of target structures formed using opposite diffraction orders of radiation diffracted in the first and second directions.

20. A method according to any preceding clause wherein in steps (b) and (c) said diffraction signals are captured while illuminating the target structures using a segmented illumination profile having illuminated regions and dark regions, each illuminated region being symmetrically opposite a dark region, when reflected in the first direction and when reflected in the second direction.

21. A method according to clause 20 wherein said segmented illumination profile has four quadrants, said illuminated regions falling only within two quadrants diametrically opposite one another.

22. A method according to clause 20 or 21 wherein said detection system is a segmented detection system, whereby the or each first image and the or each second image, includes complementary portions which are images of the target structure structures formed using opposite diffraction orders of the radiation diffracted by the target structure.

23. A method according to any preceding clause wherein each of said target structures is formed in two or more layers, said first features and second features being formed in different ones of said layers.

24. A method according to any preceding clause wherein said plurality of target structures comprises four target structures arranged together in a rectangular layout divided into similar quarters.

25. A method according to any preceding clause further comprising using the determined property to modify a metrology recipe for measuring further target structures.

26. A method according to any preceding clause further comprising using the determined property to control a lithographic apparatus to apply patterns to substrates.

27. An inspection apparatus for determining overlay performance of a lithographic process, the inspection apparatus comprising:

a support for a substrate on which are provided a plurality of target structures that have been formed by the lithographic process, each target structure comprising a set of first features arranged periodically in at least a first direction and a set of second features arranged periodically in at least the first direction and being subject to overlay error in the placement of the second features relative to the first features, an illumination system and a detection system which are together operable to capture first diffraction signals comprising selected portions of radiation diffracted by at least a subset of the target structures and second diffraction signals comprising selected portions of radiation diffracted by at least a subset of the overlay targets;

a processor for processing asymmetry information derived from the first diffraction signals and the second diffraction signals to calculate at least a measurement of said overlay error in at least the first direction, wherein said processor is operable on the basis that said target structures have been formed with programmed offsets in the placement of the second features relative to the first features in addition to said overlay error, the programmed offsets within each subset differing in both the first direction and in a second direction, the first and second directions being non-parallel, and said processor is arranged to calculate overlay error by combining said asymmetry information with knowledge of said programmed offsets while making no assumption whether asymmetry in a given target structure results from relative displacement of the second features in the first direction, in the second direction or both directions.

28. An inspection apparatus according to clause 27 wherein the illumination system and the detection system are configured such that said first diffraction signals are captured under first capture conditions and the second diffraction signals are captured under second capture conditions different from the first capture conditions.

29. An inspection apparatus according to clause 28 wherein said first capture conditions and said second capture conditions differ in one or more of the wavelength, polarization, and angular distribution of radiation used for illumination and/or detection of the target structures.

30. An inspection apparatus according to clause 27, 28 or 29 wherein the first diffraction signals comprise radiation diffracted by a first subset of target structures and the second diffraction signals comprise radiation diffracted by a second subset of target structures different from the first subset of target structures.

31. An inspection apparatus according to any of clauses 27 to 30 wherein the processor is arranged to calculate overlay error by deriving from the first diffraction signals a first asymmetry value for each of at least four target structures, by deriving from the second diffraction signals a second asymmetry value for each of at least four target structures, and by using at least the derived first and second asymmetry values to solve equations in more than four unknowns, one of said unknowns being the measurement of overlay error in the first direction.

32. An inspection apparatus according to any of clauses 27 to 30 wherein the processor is arranged to calculate overlay error by deriving from the first and second diffraction signals an asymmetry value for five or more target structures, and to use at least the derived asymmetry values to solve equations in more than four unknowns, one of said unknowns being the measurement of overlay error in the first direction.

33. An inspection apparatus according to clause 32 wherein the processor is arranged to calculate overlay error by deriving from the first and second diffraction signals an asymmetry value for seven or more target structures, and to use at least the derived first and second asymmetry values to solve equations in more than four unknowns, one of said unknowns being the measurement of overlay error in the first direction.

34. An inspection apparatus according to any of clauses 27 to 33 wherein the illumination system and the detection system are further operable together to capture third diffraction signals comprising selected portions of radiation diffracted by at least a subset of the overlay targets, and wherein the processor is arranged to process asymmetry information derived from the first diffraction signals, the second diffraction signals and the third diffraction signals to calculate a measurement of said overlay error in at least the first direction.

35. An inspection apparatus according to clause 34 wherein the processor is arranged to calculate overlay error by using the first diffraction signals to derive an asymmetry value for each of at least four target structures, by using the second diffraction signals to derive an asymmetry value for each of at least four target structures and by using the third diffraction signals to derive an asymmetry value for each of at least three target structures, and by using more than eight of the derived asymmetry values to solve equations in more than eight unknowns, one of said unknowns being the measurement of overlay error in the first direction.

36. An inspection apparatus according to any of clauses 31 to 35 wherein the processor is arranged also to calculate a measurement of overlay error in the second direction.

37. An inspection apparatus according to any of clauses 27 to 35 wherein the illumination system and detection system are operable to capture said first diffraction signals for said plurality of target structures in the form of one or more first images of the plurality of target structures and also operable to capture said second diffraction signals for the plurality of target structures in the form of one or more second images of the plurality of target structures, and wherein the processor is arranged to derive a first asymmetry value for each target structure from intensity values in respective portions of said first image or images and to derive a second asymmetry value from intensity values in respective portions of said second image or images.

38. An inspection apparatus according to clause 37 wherein each of said first and second images contains complementary portions which are images of the same plurality of target structures formed using opposite diffraction orders of radiation diffracted in the first and second directions.

39. An inspection apparatus according to any of clauses 27 to 38 wherein said illumination system is operable to illuminate the target structures using a segmented illumination profile having illuminated regions and dark regions, each illuminated region being symmetrically opposite a dark region, when reflected in the first direction and when reflected in the second direction.

40. An inspection apparatus according to clause 39 wherein said segmented illumination profile has four quadrants, said illuminated regions falling only within two quadrants diametrically opposite one another.

41. An inspection apparatus according to clause 39 or 40 wherein said detection system is a segmented detection system, whereby the or each first image and the or each second image, includes complementary portions which are images of the target structure structures formed using opposite diffraction orders of radiation diffracted by the target structure.

42. A metrology target for use in a method according to any of clauses 1 to 26 wherein said metrology target includes at least four target structures, each target structure comprising first features periodic in both a first direction and a second direction and second features periodic in both the first direction and the second direction, the first and second directions being non-parallel, and wherein said target structures have programmed offsets in placement of the second features relative to the first features in both the first direction and the second direction, each target structure within said at least four target structures having a different combination of programmed offset in the first and second directions.

43. A metrology target according to clause 42 wherein each of said target structures is formed in two or more layers, said first features and second features being formed in different ones of said layers.

44. A metrology target according to clause 42 or 43 wherein said at least four target structures are arranged together in a rectangular layout divided into similar quarters.

45. A metrology target according to clause 42, 43 or 44 wherein the metrology target includes a first subset of said target structures and a second subset of said target structures, each subset comprising at least four target structures having a different combination of programmed offset in the first and second directions, the second subset of target structures being different from the first subset of target structures.

46. A metrology target according to clause 45 wherein the target structures of said first subset and the target structures of said second subset differ in one or more of pitch, feature size, relative placement, and segmentation in the second direction.

47. A metrology target according to clause 45 wherein the target structures of said first subset and the target structures of said second subset differ only in the combinations of programmed offsets in both the first direction and the second direction, the number of combinations of programmed offsets available over both subsets being greater than four.

48. A metrology target according to clause 47 wherein target structures of the first and second subsets are arranged together a composite metrology target, the layout of target structures being such that a bias vector defined by the programmed offsets in the first and second directions varies progressively from each target structure to its neighbors.

49. A metrology target according to any of clauses 42 to 48 wherein each of said first features and said second features comprises a feature whose dimension is the same in the first direction as in the second direction.

50. A metrology target according to any of clauses 42 to 49 wherein the first features of at least the first subset of target structures are formed in a first continuous array and the second features of the first subset of target structures are formed in a second continuous array of features, the different target structures being defined by variation of said positional offsets over one or other of said continuous arrays.

51. A processing device arranged to receive at least first and second diffraction signals captured from a plurality of target structures and to derive a measurement of overlay error in at least a first direction by performing the step (d) in the method of any of clauses 1 to 26.

52. A processing device according to clause 51 arranged to receive said first diffraction signals in the form of one or more first images of said plurality of target structures and to receive said second diffraction signals in the form of one or more second images of said plurality of target structures.

53. A computer program product comprising machine readable instructions for causing a programmable processing device to receive at least first and second diffraction signals captured from a plurality of target structures and to derive a measurement of overlay error in at least a first direction by performing the step (d) in the method of any of clauses 1 to 26.

54. A computer program product according to clause 42 wherein said machine readable instructions are further arranged to cause the programmable processing device to control automatically the operation of an inspection apparatus to cause capture of the first and second diffraction signals by steps (b) and (c) of the method.

55. A lithographic system comprising:
a lithographic apparatus for applying a pattern onto one or more substrates;
an inspection apparatus according to any of clauses 27 to 41; and
a control system for controlling the lithographic apparatus using the measurement results from the inspection apparatus, when applying the pattern to further substrates.

56. A method of manufacturing devices wherein a device pattern is applied to a series of substrates using a lithographic process, the method including overlay error using a plurality of target structures formed as part of or beside said device pattern on at least one of said substrates using a method according to any of clauses 1 to 26, and controlling the lithographic process for later substrates in accordance with the result of the measuring.

57. A metrology target for use in overlay metrology, said metrology target including a plurality of target structures, each target structure comprising first features periodic in both a first direction and a second direction and second features periodic in both the first direction and the second direction, the first and second directions being non-parallel, and wherein different ones of said target structures have different programmed offsets in placement of the second features relative to the first features in both the first direction and the second direction, and wherein said target structures are arranged into said metrology target such that any target structure bordering two neighboring target structures has a programmed offset intermediate between the programmed offsets of those two neighboring target structures.

58. A metrology target according to clause 57 wherein a bias vector representing said programmed offset rotates less than ninety degrees between neighboring target structures.

59. A metrology target according to clause 58 wherein a bias vector representing said programmed offset rotates 45 degrees between neighboring target structures.

60. A metrology target according to any of clauses 57 to 59 wherein five or more of said target structures are arranged in a closed ring.

61. A metrology target according to any of clauses 57 to 60 wherein eight or more of said target structures are arranged in said closed ring.

62. A metrology target according to any of clauses 57 to 61 wherein five or more of said target structures are arranged in a line.

63. A metrology target according to any of clauses 57 to 62 wherein seven or more of said target structures are arranged in a line.

64 A set of patterning devices for use in a lithographic process, the patterning devices including at least a first patterning device configured to define the first features of a metrology target according to any of clauses 57 to 63 and a second patterning device configured for to define the second features of the metrology target.

65. A set of patterning devices according to clause 64 wherein the first features of said target structures are formed in a first continuous array and the second features of the first subset of target structures are formed in a second continuous array of features, the different target structures being defined by variation of said positional offsets over one or other of said continuous arrays.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 1-100 nm), as well as particle beams, such as ion beams or electron beams. Implementations of scatterometers and other inspection apparatus can be made in UV and EUV wavelengths using suitable sources, and the present disclosure is in no way limited to systems using IR and visible radiation.

The term "lens", where the context allows, may refer to any one or combination of various types of optical components, including refractive, reflective, magnetic, electromagnetic and electrostatic optical components. Reflective components are likely to be used in an apparatus operating in the UV and/or EUV ranges.

The breadth and scope of the present invention should not be limited by any of the above-described exemplary embodiments, but should be defined only in accordance with the following claims and their equivalents.

The invention claimed is:

1. A method of determining overlay performance of a lithographic process, the method comprising:
   (a) directing radiation at a plurality of target structures that have been formed by the lithographic process, each target structure comprising a set of first features arranged periodically in at least a first direction and a set of second features arranged periodically in at least the first direction and being subject to overlay error associated with the second features relative to the first features,
   (b) using a detection system to detect first diffraction signals comprising selected portions of the radiation diffracted by at least a subset of the plurality of target structures;
   (c) using the detection system to detect second diffraction signals comprising selected portions of the radiation diffracted by at least a subset of the plurality of target structures; and
   (d) processing asymmetry information derived from the first diffraction signals and the second diffraction signals to calculate at least a measurement of the overlay error in at least the first direction,
   wherein said target structures have been formed with programmed offsets in the placement of the second features relative to the first features in addition to said overlay error, the programmed offsets within each subset differing in both the first direction and in a second direction, the first and second directions being non-parallel,
   wherein the calculation of overlay error in step (d) combines said asymmetry information with knowledge of the programmed offsets while making no assumption whether asymmetry in a given target structure results from relative displacement of the second features in the first direction, in the second direction or both directions, and
   wherein in step (b) said first diffraction signals for said plurality of target structures are captured using the detection system to form one or more first images of the plurality of target structures,
   wherein in step (c) said second diffraction signals for the plurality of target structures are captured using the detection system to form one or more second images of the plurality of target structures, and
   wherein in step (d) a first asymmetry value for each target structure is derived from intensity values in respective portions of the first image or images and a second asymmetry value is derived from intensity values in respective portions of the second image or images.

2. The method of claim 1, wherein the first diffraction signals are captured in step (b) under first capture conditions and the second diffraction signals are captured in step (c) under second capture conditions different from the first capture conditions.

3. The method of claim 2, wherein said first capture conditions and said second capture conditions differ in one or more of wavelength, polarization, and angular distribution of radiation used for illumination and/or detection of the target structures.

4. The method of claim 1, wherein the first diffraction signals captured in step (b) comprise radiation diffracted by the first subset of target structures and the second diffraction signals captured in step (c) comprise radiation diffracted by a second subset of target structures different from the first subset of target structures.

5. The method of claim 4, wherein the target structures of the first subset and the target structures of the second subset differ in one or more of pitch, feature size, relative placement, and segmentation in the second direction.

6. The method of claim 1, wherein each of the first features and said second features comprises an elongate feature extending transverse to the first direction and being segmented periodically in the second direction.

7. The method of claim 6, wherein the segmentation of the elongate first and second features has a period different to a period of spacing of the first and second features.

8. The method of claim 1, wherein the calculation of overlay error in step (d) derives from the first diffraction signals a first asymmetry value for each of at least four target structures and derives from the second diffraction signals a second asymmetry value for each of at least four target structures, and uses at least the derived first and second asymmetry values to solve equations in more than four unknowns, one of the unknowns being the measurement of overlay error in the first direction.

9. The method of claim 8, wherein the calculation of overlay error in step (d) calculates a measurement of overlay error in the second direction.

10. The method of claim 1, further comprising a step:
using the detection system to capture third diffraction signals comprising selected portions of radiation diffracted by at least a subset of the plurality of target structures,
and wherein the step (d) includes processing asymmetry information derived from the first diffraction signals, the second diffraction signals, and the third diffraction signals to calculate a measurement of the overlay error in at least the first direction.

11. The method of claim 10, wherein the calculation of overlay error in step (d) uses the first diffraction signals to derive an asymmetry value for each of at least four target structures, uses the second diffraction signals to derive an asymmetry value for each of at least four target structures, and uses the third diffraction signals to derive an asymmetry value for each of at least three target structures, and uses more than eight of the derived asymmetry values to solve equations in more than eight unknowns, one of the unknowns being the measurement of overlay error in the first direction.

12. The method of claim 1, wherein each of the first and second images contains complementary portions that are images of the same plurality of target structures formed using opposite diffraction orders of radiation diffracted in the first and second directions.

13. A method of determining overlay performance of a lithographic process, the method comprising:
(a) directing radiation at a plurality of target structures that have been formed by the lithographic process, each target structure comprising a set of first features arranged periodically in at least a first direction and a set of second features arranged periodically in at least the first direction and being subject to overlay error associated with the second features relative to the first features,
(b) using a detection system to detect first diffraction signals comprising selected portions of the radiation diffracted by at least a subset of the plurality of target structures;
(c) using the detection system to detect second diffraction signals comprising selected portions of the radiation diffracted by at least a subset of the plurality of target structures; and
(d) processing asymmetry information derived from the first diffraction signals and the second diffraction signals to calculate at least a measurement of the overlay error in at least the first direction,
wherein said target structures have been formed with programmed offsets in the placement of the second features relative to the first features in addition to said overlay error, the programmed offsets within each subset differing in both the first direction and in a second direction, the first and second directions being non-parallel,
wherein the calculation of overlay error in step (d) combines said asymmetry information with knowledge of the programmed offsets while making no assumption whether asymmetry in a given target structure results from relative displacement of the second features in the first direction, in the second direction or both directions, and
wherein in steps (b) and (c) said diffraction signals are captured while illuminating the target structures using a segmented illumination profile having illuminated regions and dark regions, each illuminated region being symmetrically opposite a dark region, when reflected in the first direction and when reflected in the second direction.

14. The method of claim 13, wherein said segmented illumination profile has four quadrants, said illuminated regions falling only within two quadrants diametrically opposite one another.

15. The method of claim 13, wherein the first diffraction signals are captured in step (b) under first capture conditions and the second diffraction signals are captured in step (c) under second capture conditions different from the first capture conditions.

16. The method of claim 13, wherein said first capture conditions and said second capture conditions differ in one or more of wavelength, polarization, and angular distribution of radiation used for illumination and/or detection of the target structures.

17. The method of claim 13, wherein the first diffraction signals captured in step (b) comprise radiation diffracted by the first subset of target structures and the second diffraction signals captured in step (c) comprise radiation diffracted by a second subset of target structures different from the first subset of target structures.

18. The method of claim 17, wherein the target structures of the first subset and the target structures of the second subset differ in one or more of pitch, feature size, relative placement, and segmentation in the second direction.

19. The method of claim 13, wherein the first features and said second features comprise respective first and second elongate features extending transverse to the first direction and being segmented periodically in the second direction.

20. The method of claim 19, wherein the segmentation of the first and second elongate features has a period different to a period of spacing of the first and second features.

21. The method of claim 13, wherein the calculation of overlay error in step (d) derives from the first diffraction signals a first asymmetry value for each of at least four target structures and derives from the second diffraction signals a second asymmetry value for each of at least four target structures, and uses at least the derived first and second asymmetry values to solve equations in more than four unknowns, one of the unknowns being the measurement of overlay error in the first direction.

22. The method of claim 21, wherein the calculation of overlay error in step (d) calculates a measurement of overlay error in the second direction.

23. The method of claim 13, further comprising:
using the detection system to capture third diffraction signals comprising selected portions of radiation diffracted by at least a subset of the plurality of target structures,
and wherein the step (d) includes processing asymmetry information derived from the first diffraction signals, the second diffraction signals, and the third diffraction signals to calculate a measurement of the overlay error in at least the first direction.

24. The method of claim 23, wherein the calculation of overlay error in step (d) uses the first diffraction signals to derive an asymmetry value for each of at least four target structures, uses the second diffraction signals to derive an asymmetry value for each of at least four target structures, and uses the third diffraction signals to derive an asymmetry value for each of at least three target structures, and uses more than eight of the derived asymmetry values to solve equations in more than eight unknowns, one of the unknowns being the measurement of overlay error in the first direction.

\* \* \* \* \*